(12) United States Patent
Johnson et al.

(10) Patent No.: US 7,819,872 B2
(45) Date of Patent: Oct. 26, 2010

(54) FLEXIBLE ENDOSCOPIC CATHETER WITH LIGASURE

(75) Inventors: Kristin D. Johnson, Louisville, CO (US); Joe D. Sartor, Longmont, CO (US); Gene H. Arts, Berthoud, CO (US); Randel A. Frazier, St. Louis, MO (US)

(73) Assignee: Covidien AG, Neuhausen am Rheinfall (CH)

( * ) Notice: Subject to any disclaimer, the term of this patent is extended or adjusted under 35 U.S.C. 154(b) by 296 days.

(21) Appl. No.: 11/540,779

(22) Filed: Sep. 29, 2006

(65) Prior Publication Data

US 2007/0078459 A1      Apr. 5, 2007

Related U.S. Application Data

(60) Provisional application No. 60/722,359, filed on Sep. 30, 2005, provisional application No. 60/722,213, filed on Sep. 30, 2005, provisional application No. 60/722,186, filed on Sep. 30, 2005.

(51) Int. Cl.
*A61B 18/14* (2006.01)

(52) U.S. Cl. .......................................... 606/51; 606/52

(58) Field of Classification Search ............. 606/32–52, 606/205–207
See application file for complete search history.

(56) References Cited

U.S. PATENT DOCUMENTS

| | | | |
|---|---|---|---|
| 371,664 A | 10/1887 | Brannan et al. | |
| 702,472 A | 6/1902 | Pignolet | |
| 728,883 A | 5/1903 | Downes | |
| 1,586,645 A | 6/1926 | Bierman | |
| 1,813,902 A | 7/1931 | Bovie | |
| 2,002,594 A | 5/1935 | Wappler et al. | |
| 2,011,169 A | 8/1935 | Wappler | |
| 2,031,682 A | 2/1936 | Wappler et al. | |
| 2,176,479 A | 10/1939 | Willis | |
| 2,305,156 A | 4/1941 | Grubel | |

(Continued)

FOREIGN PATENT DOCUMENTS

CA         2104423         2/1994

(Continued)

OTHER PUBLICATIONS

Int'l Search Report EP 06 020574.7 dated Sep. 21, 2007.

(Continued)

*Primary Examiner*—Michael Peffley
*Assistant Examiner*—Ronald Hupczey, Jr.

(57) ABSTRACT

An endoscopic forceps is disclosed including an end effector assembly having two jaw members movable from a first position in spaced relation relative to one another to at least a second position closer to one another for grasping tissue therebetween. Each of the jaw members is connectable to an electrosurgical energy source for conducting energy through tissue held therebetween. The jaw members are biased to the first position. The end effector assembly of the endoscopic forceps further includes a wire snare having a proximal end connectable to an electrosurgical energy source and a distal end translatably extending out of one of the jaw members and operatively associated with the other of the jaw members. In use, withdrawal of the proximal end of the wire snare results in movement of the jaw members from the first position to a second position and clamping of the tissue between the jaws.

9 Claims, 9 Drawing Sheets

U.S. PATENT DOCUMENTS

| | | | |
|---|---|---|---|
| 2,279,753 A | 4/1942 | Knopp | |
| 2,632,661 A | 8/1948 | Cristofv | |
| 2,668,538 A | 2/1954 | Baker | |
| 2,796,065 A | 6/1957 | Kapp | |
| 3,459,187 A | 8/1969 | Pallotta | |
| 3,643,663 A | 2/1972 | Sutter | |
| 3,651,811 A | 3/1972 | Hildebrandt et al. | |
| 3,720,896 A | 3/1973 | Beierlein | |
| 3,862,630 A | 1/1975 | Balamuth | |
| 3,863,339 A | 2/1975 | Reaney et al. | |
| 3,866,610 A | 2/1975 | Kletschka | |
| 3,911,766 A | 10/1975 | Fridolph et al. | |
| 3,920,021 A | 11/1975 | Hiltebrandt | |
| 3,921,641 A | 11/1975 | Hulka | |
| 3,938,527 A | 2/1976 | Rioux et al. | |
| 3,952,749 A | 4/1976 | Fridolph et al. | |
| 3,970,088 A | 7/1976 | Morrison | |
| 3,987,795 A | 10/1976 | Morrison | |
| 4,005,714 A | 2/1977 | Hiltebrandt | |
| 4,041,952 A | 8/1977 | Morrison, Jr. et al. | |
| 4,074,718 A | 2/1978 | Morrison, Jr. | |
| 4,088,134 A | 5/1978 | Mazzariello | |
| 4,112,950 A | 9/1978 | Pike | |
| 4,127,222 A | 11/1978 | Adams | |
| 4,128,099 A | 12/1978 | Bauer | |
| 4,165,746 A | 8/1979 | Burgin | |
| 4,233,734 A | 11/1980 | Bies | |
| 4,300,564 A | 11/1981 | Furihata | |
| D263,020 S | 2/1982 | Rau, III | |
| 4,370,980 A | 2/1983 | Lottick | |
| 4,375,218 A | 3/1983 | DiGeronimo | |
| 4,416,276 A | 11/1983 | Newton et al. | |
| 4,418,692 A | 12/1983 | Guay | |
| 4,452,246 A | 6/1984 | Bader et al. | |
| 4,492,231 A | 1/1985 | Auth | |
| 4,552,143 A | 11/1985 | Lottick | |
| 4,574,804 A | 3/1986 | Kurwa | |
| 4,597,379 A | 7/1986 | Kihn et al. | |
| 4,600,007 A | 7/1986 | Lahodny et al. | |
| 4,655,215 A | 4/1987 | Pike | |
| 4,655,216 A | 4/1987 | Tischer | |
| 4,657,016 A | 4/1987 | Garito et al. | |
| 4,662,372 A | 5/1987 | Sharkany et al. | |
| 4,671,274 A | 6/1987 | Sorochenko | |
| 4,685,459 A | 8/1987 | Koch et al. | |
| D295,893 S | 5/1988 | Sharkany et al. | |
| D295,894 S | 5/1988 | Sharkany et al. | |
| 4,754,892 A | 7/1988 | Retief | |
| 4,763,669 A | 8/1988 | Jaeger | |
| 4,827,929 A | 5/1989 | Hodge | |
| 4,846,171 A | 7/1989 | Kauphusman et al. | |
| 4,887,612 A | 12/1989 | Esser et al. | |
| 4,938,761 A | 7/1990 | Ensslin | |
| 4,985,030 A | 1/1991 | Melzer et al. | |
| 5,007,908 A | 4/1991 | Rydell | |
| 5,026,370 A | 6/1991 | Lottick | |
| 5,035,695 A | 7/1991 | Weber, Jr. et al. | |
| 5,084,057 A | 1/1992 | Green et al. | |
| 5,099,840 A | 3/1992 | Goble et al. | |
| 5,116,332 A | 5/1992 | Lottick | |
| 5,147,357 A | 9/1992 | Rose et al. | |
| 5,151,102 A | 9/1992 | Kamiyama et al. | |
| 5,176,695 A | 1/1993 | Dulebohn | |
| 5,190,541 A | 3/1993 | Abele et al. | |
| 5,196,009 A | 3/1993 | Kirwan, Jr. | |
| 5,197,964 A | 3/1993 | Parins | |
| 5,207,686 A | 5/1993 | Dolgin | |
| 5,215,101 A | 6/1993 | Jacobs et al. | |
| 5,217,457 A | 6/1993 | Delahuerga et al. | |
| 5,217,458 A | 6/1993 | Parins | |
| 5,217,460 A | 6/1993 | Knoepfler | |
| 5,219,354 A | 6/1993 | Choudhury et al. | |
| 5,244,462 A | 9/1993 | Delahuerga et al. | |
| 5,250,047 A | 10/1993 | Rydell | |
| 5,250,063 A | 10/1993 | Abidin et al. | |
| 5,258,001 A | 11/1993 | Corman | |
| 5,258,006 A | 11/1993 | Rydell et al. | |
| 5,261,918 A | 11/1993 | Phillips et al. | |
| 5,275,615 A | 1/1994 | Rose | |
| 5,277,201 A | 1/1994 | Stern | |
| 5,282,799 A | 2/1994 | Rydell | |
| 5,290,286 A | 3/1994 | Parins | |
| 5,304,203 A | 4/1994 | El-Mallawany et al. | |
| 5,308,357 A | 5/1994 | Lichtman | |
| 5,314,445 A | 5/1994 | Degwitz et al. | |
| 5,318,589 A | 6/1994 | Lichtman | |
| 5,324,289 A | 6/1994 | Eggers | |
| 5,326,806 A | 7/1994 | Yokoshima et al. | |
| 5,330,471 A | 7/1994 | Eggers | |
| 5,334,183 A | 8/1994 | Wuchinich | |
| 5,334,215 A | 8/1994 | Chen | |
| 5,336,220 A | 8/1994 | Ryan et al. | |
| 5,336,221 A | 8/1994 | Anderson | |
| 5,342,359 A | 8/1994 | Rydell | |
| 5,342,381 A | 8/1994 | Tidemand | |
| 5,342,393 A | 8/1994 | Stack | |
| 5,344,424 A | 9/1994 | Roberts et al. | |
| 5,352,222 A | 10/1994 | Rydell | |
| 5,354,271 A | 10/1994 | Voda | |
| 5,356,408 A | 10/1994 | Rydell | |
| 5,366,477 A | 11/1994 | LeMarie, III et al. | |
| 5,368,600 A | 11/1994 | Failla et al. | |
| 5,376,089 A | 12/1994 | Smith | |
| 5,383,897 A | 1/1995 | Wholey | |
| 5,389,098 A | 2/1995 | Tsuruta et al. | |
| 5,389,104 A | 2/1995 | Hahnen et al. | |
| 5,391,166 A | 2/1995 | Eggers | |
| 5,391,183 A | 2/1995 | Janzen et al. | |
| 5,396,900 A | 3/1995 | Slater et al. | |
| 5,403,312 A | 4/1995 | Yates et al. | |
| 5,411,519 A | 5/1995 | Tovey et al. | |
| 5,411,520 A | 5/1995 | Nash et al. | |
| 5,413,571 A | 5/1995 | Katsaros et al. | |
| 5,415,657 A | 5/1995 | Taymor-Luria | |
| 5,422,567 A | 6/1995 | Matsunaga | |
| 5,423,810 A | 6/1995 | Goble et al. | |
| 5,425,690 A | 6/1995 | Chang | |
| 5,425,739 A | 6/1995 | Jessen | |
| 5,429,616 A | 7/1995 | Schaffer | |
| 5,431,672 A | 7/1995 | Cote et al. | |
| 5,431,674 A | 7/1995 | Basile et al. | |
| 5,437,292 A | 8/1995 | Kipshidze et al. | |
| 5,438,302 A | 8/1995 | Goble | |
| 5,441,517 A | 8/1995 | Kensey et al. | |
| 5,443,463 A | 8/1995 | Stern et al. | |
| 5,443,464 A | 8/1995 | Russell et al. | |
| 5,443,480 A | 8/1995 | Jacobs et al. | |
| 5,445,638 A | 8/1995 | Rydell et al. | |
| 5,445,658 A | 8/1995 | Durrfeld et al. | |
| 5,451,224 A | 9/1995 | Goble et al. | |
| 5,456,684 A | 10/1995 | Schmidt et al. | |
| 5,458,598 A | 10/1995 | Feinberg et al. | |
| 5,460,629 A | 10/1995 | Shlain et al. | |
| 5,462,546 A | 10/1995 | Rydell | |
| 5,472,443 A | 12/1995 | Cordis et al. | |
| 5,478,351 A | 12/1995 | Meade et al. | |
| 5,480,409 A | 1/1996 | Riza | |
| 5,484,436 A | 1/1996 | Eggers et al. | |
| 5,496,312 A | 3/1996 | Klicek | |
| 5,496,317 A | 3/1996 | Goble et al. | |
| 5,496,347 A | 3/1996 | Hashiguchi et al. | |
| 5,499,997 A | 3/1996 | Sharpe et al. | |
| 5,509,922 A | 4/1996 | Aranyi et al. | |
| 5,514,134 A | 5/1996 | Rydell et al. | |

| Patent No. | Date | Inventor(s) |
|---|---|---|
| 5,527,313 A | 6/1996 | Scott et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,715 A | 7/1996 | Katsaros et al. |
| 5,542,945 A | 8/1996 | Fritzsch |
| 5,558,671 A | 9/1996 | Yates |
| 5,558,672 A | 9/1996 | Edwards et al. |
| 5,562,699 A | 10/1996 | Heimberger et al. |
| 5,569,241 A | 10/1996 | Edwardds |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,805 A | 11/1996 | Li |
| 5,578,052 A | 11/1996 | Koros et al. |
| 5,582,611 A | 12/1996 | Tsuruta et al. |
| 5,585,896 A | 12/1996 | Yamazaki et al. |
| 5,590,570 A | 1/1997 | LeMaire, III et al. |
| 5,601,601 A | 2/1997 | Tal et al. |
| 5,603,711 A | 2/1997 | Parins et al. |
| 5,603,723 A | 2/1997 | Aranyi et al. |
| 5,611,798 A | 3/1997 | Eggers |
| 5,620,453 A | 4/1997 | Nallakrishnan |
| 5,620,459 A * | 4/1997 | Lichtman .................. 606/205 |
| 5,624,452 A | 4/1997 | Yates |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,638,003 A | 6/1997 | Hall |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,658,281 A | 8/1997 | Heard |
| 5,662,667 A | 9/1997 | Knodel |
| 5,665,100 A | 9/1997 | Yoon |
| 5,667,526 A | 9/1997 | Levin |
| 5,674,220 A | 10/1997 | Fox et al. |
| 5,681,282 A | 10/1997 | Eggers et al. |
| 5,688,270 A | 11/1997 | Yates et al. |
| 5,693,051 A | 12/1997 | Schulze et al. |
| 5,695,522 A | 12/1997 | LeMaire, III et al. |
| 5,700,261 A | 12/1997 | Brinkerhoff |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| 5,735,848 A | 4/1998 | Yates et al. |
| 5,743,906 A | 4/1998 | Parins et al. |
| 5,755,717 A | 5/1998 | Yates et al. |
| 5,766,130 A | 6/1998 | Selmonosky |
| 5,766,166 A | 6/1998 | Hooven |
| 5,766,170 A | 6/1998 | Eggers |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,779,701 A | 7/1998 | McBrayer et al. |
| H1745 H | 8/1998 | Paraschac |
| 5,792,137 A | 8/1998 | Carr et al. |
| 5,792,177 A | 8/1998 | Kaseda |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,800,449 A | 9/1998 | Wales |
| 5,807,393 A | 9/1998 | Williamson, IV et al. |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,817,093 A | 10/1998 | Williamson, IV et al. |
| 5,820,630 A | 10/1998 | Lind |
| 5,827,271 A | 10/1998 | Buysse et al. |
| 5,827,279 A | 10/1998 | Hughett et al. |
| 5,827,281 A | 10/1998 | Levin |
| 5,827,323 A * | 10/1998 | Klieman et al. ............ 606/205 |
| 5,827,548 A | 10/1998 | Lavallee et al. |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,860,976 A | 1/1999 | Billings et al. |
| 5,876,401 A | 3/1999 | Schulze et al. |
| 5,882,567 A | 3/1999 | Cavallaro et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,984 A | 7/1999 | Sutcu et al. |
| 5,925,043 A | 7/1999 | Kumar et al. |
| 5,935,126 A | 8/1999 | Riza |
| 5,944,718 A | 8/1999 | Austin et al. |
| 5,951,549 A | 9/1999 | Richardson et al. |
| 5,954,720 A | 9/1999 | Wilson et al. |
| 5,957,923 A | 9/1999 | Hahnen et al. |
| 5,960,544 A | 10/1999 | Beyers |
| 5,961,514 A | 10/1999 | Long et al. |
| 5,964,758 A | 10/1999 | Dresden |
| 5,976,132 A | 11/1999 | Morris |
| 5,984,938 A * | 11/1999 | Yoon ........................ 606/170 |
| 5,984,939 A | 11/1999 | Yoon |
| 5,989,264 A | 11/1999 | Wright |
| 5,989,277 A | 11/1999 | LeMaire, III et al. |
| 5,997,565 A | 12/1999 | Inoue |
| 6,004,335 A | 12/1999 | Vaitekunas et al. |
| 6,010,516 A | 1/2000 | Hulka et al. |
| 6,024,741 A | 2/2000 | Williamson et al. |
| 6,024,744 A | 2/2000 | Kese et al. |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,074,386 A | 6/2000 | Goble et al. |
| RE36,795 E | 7/2000 | Rydell |
| 6,083,223 A | 7/2000 | Baker |
| 6,086,586 A | 7/2000 | Hooven |
| 6,090,107 A | 7/2000 | Borgmeier et al. |
| 6,096,037 A | 8/2000 | Mulier et al. |
| 6,099,550 A | 8/2000 | Yoon |
| 6,102,909 A | 8/2000 | Chen et al. |
| 6,110,171 A | 8/2000 | Rydell |
| 6,113,596 A | 9/2000 | Hooven et al. |
| 6,113,598 A | 9/2000 | Baker |

| | | |
|---|---|---|
| 6,117,158 A | 9/2000 | Measamer et al. |
| 6,123,701 A | 9/2000 | Nezhat |
| H1904 H | 10/2000 | Yates et al. |
| 6,126,658 A | 10/2000 | Baker |
| 6,152,923 A | 11/2000 | Ryan |
| 6,162,220 A | 12/2000 | Nezhat |
| 6,174,309 B1 | 1/2001 | Wrublewski et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,217,602 B1 | 4/2001 | Redmon |
| 6,221,039 B1 | 4/2001 | Durgin et al. |
| 6,224,593 B1 | 5/2001 | Ryan et al. |
| 6,228,080 B1 | 5/2001 | Gines |
| 6,228,083 B1 | 5/2001 | Lands et al. |
| 6,235,026 B1 | 5/2001 | Smith |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,302,424 B1 | 10/2001 | Gisinger et al. |
| 6,319,451 B1 | 11/2001 | Brune |
| 6,322,561 B1 | 11/2001 | Eggers et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,268 B1 | 3/2002 | Hunt et al. |
| D457,958 S | 5/2002 | Dycus et al. |
| D457,959 S | 5/2002 | Tetzlaff et al. |
| 6,383,194 B1 | 5/2002 | Pothula |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,500,176 B1 | 12/2002 | Truckai et al. |
| 6,511,480 B1 | 1/2003 | Tetzlaff et al. |
| 6,514,252 B2 | 2/2003 | Nezhat et al. |
| 6,527,771 B1 | 3/2003 | Weadock et al. |
| 6,558,385 B1 | 5/2003 | McClurken et al. |
| 6,562,037 B2 | 5/2003 | Paton et al. |
| 6,585,735 B1 | 7/2003 | Lands et al. |
| 6,602,252 B2 | 8/2003 | Mollenauer |
| 6,616,654 B2 | 9/2003 | Mollenauer |
| 6,616,658 B2 | 9/2003 | Ineson |
| 6,616,659 B1 | 9/2003 | de la Torre et al. |
| 6,616,661 B2 | 9/2003 | Wellman et al. |
| 6,620,161 B2 | 9/2003 | Schulze et al. |
| 6,626,901 B1 | 9/2003 | Treat et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,177 B2 | 12/2003 | Truckai et al. |
| 6,660,072 B2 | 12/2003 | Chatterjee |
| 6,669,696 B2 | 12/2003 | Bacher et al. |
| 6,676,660 B2 | 1/2004 | Wampler et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,695,840 B2 | 2/2004 | Schulze |
| 6,702,810 B2 | 3/2004 | McClurken et al. |
| 6,726,068 B2 | 4/2004 | Miller |
| 6,726,686 B2 | 4/2004 | Buysse et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,757,977 B2 | 7/2004 | Dambal et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,775,575 B2 | 8/2004 | Bommannan et al. |
| 6,776,780 B2 | 8/2004 | Mulier et al. |
| 6,790,217 B2 | 9/2004 | Schulze et al. |
| 6,796,981 B2 | 9/2004 | Wham et al. |
| D496,997 S | 10/2004 | Dycus et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,860,880 B2 | 3/2005 | Treat et al. |
| 6,887,240 B1 | 5/2005 | Lands et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| 6,942,662 B2 | 9/2005 | Goble et al. |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,977,495 B2 | 12/2005 | Donofrio |
| 6,979,786 B2 | 12/2005 | Aukland et al. |
| 6,994,707 B2 | 2/2006 | Ellman et al. |
| 6,994,709 B2 | 2/2006 | Iida |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,496 B2 | 5/2006 | Yamauchi |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,112,199 B2 | 9/2006 | Cosmescu |
| D531,311 S | 10/2006 | Guerra et al. |
| 7,115,123 B2 | 10/2006 | Knowlton et al. |

| | | | | | | |
|---|---|---|---|---|---|---|
| 7,118,570 | B2 | 10/2006 | Tetzlaff et al. | 2004/0116924 A1 | 6/2004 | Dycus et al. |
| 7,118,587 | B2 | 10/2006 | Dycus et al. | 2004/0116979 A1 | 6/2004 | Truckai et al. |
| 7,131,860 | B2 | 11/2006 | Sartor et al. | 2004/0122423 A1 | 6/2004 | Dycus et al. |
| 7,131,970 | B2 | 11/2006 | Moses et al. | 2004/0143263 A1 | 7/2004 | Schechter et al. |
| 7,131,971 | B2 | 11/2006 | Dycus et al. | 2004/0147925 A1 | 7/2004 | Buysse et al. |
| 7,135,020 | B2 | 11/2006 | Lawes et al. | 2004/0162557 A1 | 8/2004 | Tetzlaff et al. |
| D533,942 | S | 12/2006 | Kerr et al. | 2004/0176762 A1 | 9/2004 | Lawes et al. |
| 7,145,757 | B2 | 12/2006 | Shea et al. | 2004/0193153 A1 | 9/2004 | Sarter et al. |
| 7,147,638 | B2 | 12/2006 | Chapman et al. | 2004/0225288 A1 | 11/2004 | Buysse et al. |
| 7,150,097 | B2 | 12/2006 | Sremcich et al. | 2004/0230189 A1 | 11/2004 | Keppel |
| 7,150,749 | B2 | 12/2006 | Dycus et al. | 2004/0236326 A1 | 11/2004 | Schulze et al. |
| D535,027 | S | 1/2007 | James et al. | 2004/0243125 A1 | 12/2004 | Dycus et al. |
| 7,156,842 | B2 | 1/2007 | Sartor et al. | 2004/0249371 A1 | 12/2004 | Dycus et al. |
| 7,156,846 | B2 | 1/2007 | Dycus et al. | 2004/0249374 A1 | 12/2004 | Tetzlaff et al. |
| 7,160,298 | B2 | 1/2007 | Lawes et al. | 2004/0250419 A1 | 12/2004 | Sremcich et al. |
| 7,160,299 | B2 | 1/2007 | Baily | 2004/0254573 A1 | 12/2004 | Dycus et al. |
| 7,169,146 | B2 | 1/2007 | Truckai et al. | 2004/0260281 A1 | 12/2004 | Baxter, III et al. |
| 7,179,258 | B2 | 2/2007 | Buysse et al. | 2005/0004564 A1 | 1/2005 | Wham et al. |
| 7,195,631 | B2 | 3/2007 | Dumbauld | 2005/0004568 A1 | 1/2005 | Lawes et al. |
| D541,418 | S | 4/2007 | Schechter et al. | 2005/0004570 A1 | 1/2005 | Chapman et al. |
| 7,207,990 | B2 | 4/2007 | Lands et al. | 2005/0021025 A1 | 1/2005 | Buysse et al. |
| D541,938 | S | 5/2007 | Kerr et al | 2005/0021026 A1 | 1/2005 | Baily |
| 7,223,265 | B2 | 5/2007 | Keppel | 2005/0021027 A1 | 1/2005 | Shields et al. |
| 7,232,440 | B2 | 6/2007 | Dumbauld et al. | 2005/0033278 A1 | 2/2005 | McClurken et al. |
| 7,241,288 | B2 | 7/2007 | Braun | 2005/0096645 A1 | 5/2005 | Wellman et al. |
| 7,241,296 | B2 | 7/2007 | Buysse et al. | 2005/0101951 A1 | 5/2005 | Wham et al. |
| 7,252,667 | B2 | 8/2007 | Moses et al. | 2005/0101952 A1 | 5/2005 | Lands et al. |
| 7,255,697 | B2 | 8/2007 | Dycus et al. | 2005/0107784 A1 | 5/2005 | Moses et al. |
| 7,267,677 | B2 | 9/2007 | Johnson et al. | 2005/0107785 A1 | 5/2005 | Dycus et al. |
| 7,270,660 | B2 | 9/2007 | Ryan | 2005/0113818 A1 | 5/2005 | Sartor et al. |
| 7,270,664 | B2 | 9/2007 | Johnson et al. | 2005/0113819 A1 | 5/2005 | Wham et al. |
| 7,276,068 | B2 | 10/2007 | Johnson et al. | 2005/0113826 A1 | 5/2005 | Johnson et al. |
| 7,300,435 | B2 | 11/2007 | Wham et al. | 2005/0113827 A1 | 5/2005 | Dumbauld et al. |
| 7,303,557 | B2 | 12/2007 | Wham et al. | 2005/0113828 A1 | 5/2005 | Shields et al. |
| 7,314,471 | B2 | 1/2008 | Holman | 2005/0119655 A1 | 6/2005 | Moses et al. |
| 7,329,256 | B2 | 2/2008 | Johnson et al. | 2005/0149017 A1 | 7/2005 | Dycus |
| 7,329,257 | B2 | 2/2008 | Kanehira et al. | 2005/0149151 A1 | 7/2005 | Orszulak et al. |
| D564,662 | S | 3/2008 | Moses et al. | 2005/0187547 A1 | 8/2005 | Sugi |
| 7,342,754 | B2 | 3/2008 | Fitzgerald et al. | 2005/0197659 A1 | 9/2005 | Bahney |
| 7,344,268 | B2 | 3/2008 | Jigamian | 2005/0203504 A1 | 9/2005 | Wham et al. |
| 7,367,976 | B2 | 5/2008 | Lawes et al. | 2005/0240179 A1 | 10/2005 | Buysse et al. |
| 2002/0013583 | A1 | 1/2002 | Camran et al. | 2006/0052778 A1 | 3/2006 | Chapman et al. |
| 2002/0049442 | A1* | 4/2002 | Roberts et al. ............... 606/50 | 2006/0064085 A1 | 3/2006 | Schechter et al. |
| 2002/0099372 | A1 | 7/2002 | Schulze et al. | 2006/0074417 A1 | 4/2006 | Cunningham et al. |
| 2002/0107517 | A1 | 8/2002 | Witt et al. | 2006/0079888 A1 | 4/2006 | Mulier et al. |
| 2002/0111624 | A1 | 8/2002 | Witt et al. | 2006/0079890 A1 | 4/2006 | Guerra |
| 2002/0188294 | A1 | 12/2002 | Couture et al. | 2006/0079891 A1 | 4/2006 | Arts et al. |
| 2003/0014052 | A1 | 1/2003 | Buysse et al. | 2006/0116675 A1 | 6/2006 | McClurken et al. |
| 2003/0014053 | A1 | 1/2003 | Nguyen et al. | 2006/0129146 A1 | 6/2006 | Dycus et al. |
| 2003/0018331 | A1 | 1/2003 | Dycus et al. | 2006/0161150 A1 | 7/2006 | Keppel |
| 2003/0018332 | A1 | 1/2003 | Schmaltz et al. | 2006/0167450 A1 | 7/2006 | Johnson et al. |
| 2003/0032956 | A1 | 2/2003 | Lands et al. | 2006/0167452 A1 | 7/2006 | Moses et al. |
| 2003/0069571 | A1 | 4/2003 | Treat et al. | 2006/0173452 A1 | 8/2006 | Buysse et al. |
| 2003/0078578 | A1 | 4/2003 | Truckai et al. | 2006/0189980 A1 | 8/2006 | Johnson et al. |
| 2003/0109875 | A1 | 6/2003 | Tetzlaff et al. | 2006/0189981 A1 | 8/2006 | Dycus et al. |
| 2003/0114851 | A1 | 6/2003 | Truckai et al. | 2006/0190035 A1 | 8/2006 | Hushka et al. |
| 2003/0139741 | A1 | 7/2003 | Goble et al. | 2006/0217709 A1 | 9/2006 | Couture et al. |
| 2003/0139742 | A1 | 7/2003 | Wampler et al. | 2006/0224158 A1 | 10/2006 | Odom et al. |
| 2003/0158549 | A1 | 8/2003 | Swanson | 2006/0259036 A1 | 11/2006 | Tetzlaff et al. |
| 2003/0181910 | A1 | 9/2003 | Dycus et al. | 2006/0264922 A1 | 11/2006 | Sartor et al. |
| 2003/0199869 | A1 | 10/2003 | Johnson et al. | 2006/0264931 A1 | 11/2006 | Chapman et al. |
| 2003/0216732 | A1 | 11/2003 | Truckai et al. | 2006/0271038 A1 | 11/2006 | Johnson et al. |
| 2003/0220637 | A1 | 11/2003 | Truckai et al. | 2006/0287641 A1 | 12/2006 | Perlin |
| 2003/0229344 | A1 | 12/2003 | Dycus et al. | 2007/0016182 A1 | 1/2007 | Lipson et al. |
| 2003/0236325 | A1 | 12/2003 | Bonora | 2007/0016187 A1 | 1/2007 | Weinberg et al. |
| 2004/0030330 | A1 | 2/2004 | Brassell et al. | 2007/0043352 A1 | 2/2007 | Garrison et al. |
| 2004/0030332 | A1 | 2/2004 | Knowlton et al. | 2007/0043353 A1 | 2/2007 | Dycus et al. |
| 2004/0049185 | A1 | 3/2004 | Latterell et al. | 2007/0055231 A1 | 3/2007 | Dycus et al. |
| 2004/0064151 | A1 | 4/2004 | Mollenauer | 2007/0060919 A1 | 3/2007 | Isaacson et al. |
| 2004/0078035 | A1 | 4/2004 | Kanehira et al. | 2007/0062017 A1 | 3/2007 | Dycus et al. |
| 2004/0082952 | A1 | 4/2004 | Dycus et al. | 2007/0074807 A1 | 4/2007 | Guerra |
| 2004/0087943 | A1 | 5/2004 | Dycus et al. | 2007/0078456 A1 | 4/2007 | Dumbauld et al. |
| 2004/0115296 | A1 | 6/2004 | Duffin | 2007/0078458 A1 | 4/2007 | Dumbauld et al. |

| | | | | | | |
|---|---|---|---|---|---|---|
| 2007/0078459 A1 | 4/2007 | Johnson et al. | | EP | 1159926 A2 | 12/2001 |
| 2007/0088356 A1 | 4/2007 | Moses et al. | | EP | 1301135 A | 4/2003 |
| 2007/0106295 A1 | 5/2007 | Garrison et al. | | EP | 1330991 A1 | 7/2003 |
| 2007/0106297 A1 | 5/2007 | Dumbauld et al. | | EP | 1486177 A2 | 6/2004 |
| 2007/0118111 A1 | 5/2007 | Weinberg | | EP | 1472984 A1 | 11/2004 |
| 2007/0118115 A1 | 5/2007 | Artale et al. | | EP | 1527744 | 5/2005 |
| 2007/0142833 A1 | 6/2007 | Dycus et al. | | EP | 1527747 A2 | 5/2005 |
| 2007/0142834 A1 | 6/2007 | Dumbauld | | EP | 1530952 A1 | 5/2005 |
| 2007/0156139 A1 | 7/2007 | Schechter et al. | | EP | 1532932 A1 | 5/2005 |
| 2007/0156140 A1 | 7/2007 | Baily | | EP | 1535581 A2 | 6/2005 |
| 2007/0173811 A1 | 7/2007 | Couture et al. | | EP | 1609430 A1 | 12/2005 |
| 2007/0173814 A1 | 7/2007 | Hixson et al. | | EP | 1632192 A1 | 3/2006 |
| 2007/0179499 A1 | 8/2007 | Garrison | | EP | 1645238 A1 | 4/2006 |
| 2007/0203485 A1 | 8/2007 | Keppel | | EP | 1645240 A2 | 4/2006 |
| 2007/0213706 A1 | 9/2007 | Dumbauld et al. | | EP | 1707143 A1 | 10/2006 |
| 2007/0213707 A1 | 9/2007 | Dumbauld et al. | | GB | 2214430 A | 6/1989 |
| 2007/0213708 A1 | 9/2007 | Dumbauld et al. | | GB | 2213416 | 8/1989 |
| 2007/0213712 A1 | 9/2007 | Buysse et al. | | JP | 501068 | 9/1984 |
| 2007/0255279 A1 | 11/2007 | Buysse et al. | | JP | 502328 | 3/1992 |
| 2007/0260235 A1 | 11/2007 | Podhajsky | | JP | 5-5106 | 1/1993 |
| 2007/0260238 A1 | 11/2007 | Guerra | | JP | 5-40112 | 2/1993 |
| 2007/0260241 A1 | 11/2007 | Dalla Betta et al. | | JP | 06343644 A2 | 12/1994 |
| 2007/0260242 A1 | 11/2007 | Dycus et al. | | JP | 07265328 A2 | 10/1995 |
| 2007/0265616 A1 | 11/2007 | Couture et al. | | JP | 08056955 A2 | 3/1996 |
| 2008/0004616 A1 | 1/2008 | Patrick | | JP | 08252263 A2 | 10/1996 |
| 2008/0009860 A1 | 1/2008 | Odom | | JP | 09010223 A2 | 1/1997 |
| 2008/0015575 A1 | 1/2008 | Odom et al. | | JP | 11244298 A2 | 9/1999 |
| 2008/0021450 A1 | 1/2008 | Couture | | JP | 2000342599 A2 | 12/2000 |
| 2008/0033428 A1 | 2/2008 | Artale et al. | | JP | 2000350732 A2 | 12/2000 |
| 2008/0039835 A1 | 2/2008 | Johnson et al. | | JP | 2001008944 A2 | 1/2001 |
| 2008/0045947 A1 | 2/2008 | Johnson et al. | | JP | 2001029356 A2 | 2/2001 |
| 2008/0058802 A1 | 3/2008 | Couture et al. | | JP | 2001128990 A2 | 5/2001 |
| 2008/0082100 A1 | 4/2008 | Orton et al. | | SU | 401367 | 11/1974 |
| | | | | WO | WO 89/00757 | 1/1989 |
| FOREIGN PATENT DOCUMENTS | | | | WO | WO 92/04873 | 4/1992 |
| | | | | WO | WO 92/06642 | 4/1992 |
| DE | 2415263 | 10/1975 | | WO | WO 94/08524 A | 4/1994 |
| DE | 2627679 | 1/1977 | | WO | WO 94/20025 | 9/1994 |
| DE | 8712328 | 3/1988 | | WO | WO 95/02369 | 1/1995 |
| DE | 4303882 | 8/1994 | | WO | WO 95/07662 | 3/1995 |
| DE | 29616210 | 1/1997 | | WO | WO 95/15124 | 6/1995 |
| DE | 19608716 | 4/1997 | | WO | WO 96/05776 | 2/1996 |
| DE | 19751106 | 5/1998 | | WO | WO 96/022056 | 7/1996 |
| DE | 19751108 | 5/1999 | | WO | WO 96/13218 | 9/1996 |
| EP | 0364216 A1 | 4/1990 | | WO | WO 97/00646 | 1/1997 |
| EP | 0518230 A1 | 12/1992 | | WO | WO 97/00647 | 1/1997 |
| EP | 0 541 930 B1 | 5/1993 | | WO | WO 97/10764 | 3/1997 |
| EP | 0572131 | 12/1993 | | WO | WO 97/24073 | 7/1997 |
| EP | 0584787 A1 | 3/1994 | | WO | WO 97/24993 | 7/1997 |
| EP | 0589453 A2 | 3/1994 | | WO | WO 98/14124 | 4/1998 |
| EP | 0623316 A1 | 11/1994 | | WO | WO 98/27880 | 7/1998 |
| EP | 0624348 A2 | 11/1994 | | WO | WO 99/03407 | 1/1999 |
| EP | 0650701 A1 | 5/1995 | | WO | WO 99/03408 | 1/1999 |
| EP | 0694290 A3 | 3/1996 | | WO | WO 99/03409 | 1/1999 |
| EP | 0717966 A1 | 6/1996 | | WO | WO 99/12488 | 3/1999 |
| EP | 0754437 A3 | 3/1997 | | WO | WO 99/40857 | 8/1999 |
| EP | 0853922 A1 | 7/1998 | | WO | WO 99/40861 | 8/1999 |
| EP | 0875209 A1 | 11/1998 | | WO | WO 99/51158 | 10/1999 |
| EP | 0878169 A1 | 11/1998 | | WO | WO 99/66850 A | 12/1999 |
| EP | 0887046 A3 | 1/1999 | | WO | WO 00/24330 | 5/2000 |
| EP | 0923907 A1 | 6/1999 | | WO | WO 00/24331 | 5/2000 |
| EP | 0986990 A1 | 3/2000 | | WO | WO 00/41638 | 7/2000 |
| EP | 1034747 A1 | 9/2000 | | WO | WO 00/47124 | 8/2000 |
| EP | 1034748 A1 | 9/2000 | | WO | WO 00/53112 | 9/2000 |
| EP | 1025807 A3 | 10/2000 | | WO | WO 01/17448 A | 3/2001 |
| EP | 1034746 A3 | 10/2000 | | WO | WO 01/54604 | 8/2001 |
| EP | 1050278 A1 | 11/2000 | | WO | WO 02/07627 | 1/2002 |
| EP | 1053719 A1 | 11/2000 | | WO | WO 02/067798 A1 | 9/2002 |
| EP | 1053720 A1 | 11/2000 | | WO | WO 02/080783 | 10/2002 |
| EP | 1055399 A1 | 11/2000 | | WO | WO 02/080784 | 10/2002 |
| EP | 1055400 A1 | 11/2000 | | WO | WO 02/080785 | 10/2002 |
| EP | 1080694 A1 | 3/2001 | | WO | WO 02/080786 | 10/2002 |
| EP | 1082944 A1 | 3/2001 | | WO | WO 02/080793 | 10/2002 |

| | | |
|---|---|---|
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/090630 A3 | 11/2003 |
| WO | WO 03/101311 | 12/2003 |
| WO | WO 2004/032776 A1 | 4/2004 |
| WO | WO 2004/032777 | 4/2004 |
| WO | WO 2004/052221 | 6/2004 |
| WO | WO 2004/073488 A2 | 9/2004 |
| WO | WO 2004/073490 | 9/2004 |
| WO | WO 2004/073753 | 9/2004 |
| WO | WO 2004/082495 | 9/2004 |
| WO | WO 2004/098383 | 11/2004 |
| WO | WO 2004/103156 | 12/2004 |
| WO | 2005/004734 A1 | 1/2005 |
| WO | WO 2005/004735 | 1/2005 |
| WO | WO 2005/009255 | 2/2005 |
| WO | WO 2005/110264 | 11/2005 |

OTHER PUBLICATIONS

Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.
Int'l Search Report EP 04 752343.6 dated Jul. 20, 2007.
Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report—Extended EP 07 009029.5 dated Jul. 12, 2007.
Int'l Search Report EP 07 009321.6 dated Aug. 17, 2007.
Int'l Search Report EP 05016399 dated Jan. 5, 2006.
Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
Int'l Search Report EP 04013772 dated Apr. 1, 2005.
Int'l Search Report EP 05013895 dated Oct. 14, 2005.
Int'l Search Report EP 05017281 dated Nov. 16, 2005.
Int'l Search Report EP 06006716 dated Aug. 4, 2006.
Int'l Search Report PCT/US01/11224 dated Nov. 13, 2001.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
Sigel et al. "The Mechanism of Blood Vessel Closure by High Frequency Electrocoagulation" Surgery Gynecology & Obstetrics, Oct. 1965 pp. 823-831.
Bergdahl et al. "Studies on Coagulation and the Development of an Automatic Computerized Bipolar Coagulator" J.Neurosurg, vol. 75, Jul. 1991, pp. 148-151.
Kennedy et al. "High-burst-strength, feedback-controlled bipolar vessel sealing" Surgical Endoscopy (1998) 12: 876-878.
Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Johnson et al. "Evaluation of the LigaSure Vessel Sealing System in Hemorrhoidectormy" American College of Surgeons (ACS) Clinicla Congress Poster (2000).
Sayfan et al. "Sutureless Closed Hemorrhoidectomy: A New Technique" Annals of Surgery vol. 234 No. 1 Jul. 2001 pp. 21-24.
Heniford at al. "Initial Results with an Electrothermal Bipolar Vessel Sealer" Surgical Endoscopy (2000) 15:799-801.
Heniford at al. "Initial Research and Clinical Results with an Electrothermal Bipolar Vessel Sealer" Oct. 1999.
McLellan at al. "Vessel Sealing for Hemostasis During Pelvic Surgery" Int'l Federation of Gynecology and Obstetrics FIGO World Congress 2000, Washington, D.C.
Levy at al. " Use of a New Energy-based Vessel Ligation Device During Vaginal Hysterectomy" Int'l Federation of Gynecology and Obstetrics (FIGO) World Congress 1999.
Crawford et al. "Use of the LigaSure Vessel Sealing System in Urologic Cancer Surger" Grand Rounds in Urology 1999 vol. 1 Issue 4 pp. 10-17.
Rothenberg at al. "Use of the LigaSure Vessel Sealing System in Minimally Invasive Surgery in Children" Int'l Pediatric Endosurgery Group (IPEG) 2000.
Palazzo et al. "Randomized clinical trial of Ligasure versus open haemorrhoidectomy" British Journal of Surgery 2002, 89, 154-157.
"Innovations in Electrosurgery" Sales/Product Literature; Dec. 31, 2000.
LigaSure Vessel Sealing System, the Seal of Confidence in General, Gynecologic, Urologic, and Laparaoscopic Surgery. Sales/Product Literature; Jan. 2004.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC 2003.
"Reducing Needlestick Injuries in the Operating Room" Sales/Product Literature 2001.
Chung at al., "Clinical Experience of Sutureless Closed Hemorrhoidectomy with LigaSure" Diseases of the Colon & Rectum vol. 46, No. 1 Jan. 2003.
Strasberg at al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Paul G. Horgan, "A Novel Technique for Parenchymal Division During Hepatectomy" The American Journal of Surgery, vol. 181, No. 3, Apr. 2001 pp. 236-237.
W. Scott Helton, "LigaSure Vessel Sealing System: Revolutionary Hemostasis Product for General Surgery" Sales/Product Literature 1999.
Michael Choti, "Abdominoperineal Resection with the LigaSure Vessel Sealing System and LigaSure Atlas 20 cm Open Instrument" Innovations That Work, Jun. 2003.
Craig Johnson, "Use of the LigaSure Vessel Sealing System in Bloodless Hemorrhoidectomy" Innovations That Work, Mar. 2000.
Muller et al., "Extended Left Hemicolectomy Using the LigaSure Vessel Sealing System" Innovations That Work, Sep. 1999.
Herman et al., "Laparoscopic Intestinal Resection With the LigaSure Vessel Sealing System: A Case Report" Innovations That Work, Feb. 2002.
Carus et al., "Initial Experience With the LigaSure Vessel Sealing System in Abdominal Surgery" Innovations That Work, Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
McLellan et al. "Vessel Sealing for Hemostasis During Gynecologic Surgery" Sales/Product Literature 1999.
Sengupta et al., "Use of a Computer-Controlled Bipolar Diathermy System in Radical Prostatectomies and Other Open Urological Surgery" ANZ Journal of Surgery (2001) 71.9 pp. 538-540.
Olsson et al. "Radical Cystectomy in Females" Current Surgical Techniques in Urology, vol. 14, Issue 3, 2001.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
E. David Crawford "Evaluation of a New Vessel Sealing Device in Urologic Cancer Surgery" Sales/Product Literature 2000.

Joseph Ortenberg "LigaSure System Used in Laparoscopic 1st and 2nd Stage Orchiopexy" Innovations That Work, Nov. 2002.
Koyle et al., "Laparoscopic Palomo Varicocele Ligation in Children and Adolescents" Pediatric Endosurgery & Innovative Techniques, vol. 6, No. 1, 2002.
Dulemba et al. "Use of a Bipolar Electrothermal Vessel Sealer in Laparoscopically Assisted Vaginal Hysterectomy" Sales/Product Literature; Jan. 2004.
Johnson et al. "Evaluation of a Bipolar electrothermal Vessel Sealing Device in Hemorrhoidectomy" Sales/Product Literature; Jan. 2004.
Int'l Search Report PCT/US98/18640 dated Dec. 17, 1998.
Int'l Search Report PCT/US98/23950 dated Dec. 29, 1998.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report EP 98944778 dated. Oct. 31, 2000.
Int'l Search Report EP 98958575.7 dated Sep. 20, 2002.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 05013463.4 dated Sep. 28, 2005.
Int'l Search Report EP 05019130.3 dated Oct. 18, 2005.
Int'l Search Report EP 05020665.5 dated Feb.16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended—EP 05021937.7 dated Mar. 6, 2006.
Int'l Search Report EP 05023017.6 date Feb. 16, 2006.
Int'l Search Report EP 05021780.1 dated Feb. 9, 2006.
Int'l Search Report EP 06002279.5 dated Mar. 22, 2006.
European Search Report dated Dec. 1, 2009.
European Search Report dated Dec. 7, 2009.

* cited by examiner

FLEXIBLE ENDOSCOPIC CATHETER WITH LIGASURE

CROSS REFERENCE TO RELATED APPLICATIONS

This application claims the benefit of and priority to each of U.S. Provisional Application No. 60/722,359, filed on Sep. 30, 2005; U.S. Provisional Application No. 60/722,213, filed on Sep. 30, 2005; and U.S. Provisional Application No. 60/722,186, filed on Sep. 30, 2005, the entire contents of each application being incorporated by reference herein.

BACKGROUND

1. Technical Field

The present disclosure relates to electrosurgical instruments and, more particularly, to flexible endoscopic bipolar electrosurgical forceps for sealing and/or cutting tissue.

2. Discussion of Related Art

Electrosurgical forceps utilize both mechanical clamping action and electrical energy to affect hemostasis by heating the tissue and blood vessels to coagulate, cauterize and/or seal tissue. As an alternative to open forceps for use with open surgical procedures, many modern surgeons use endoscopes and endoscopic instruments for remotely accessing organs through smaller, puncture-like incisions. As a direct result thereof, patients tend to benefit from less scarring and reduced healing time.

Many surgical procedures may be completed through intra-luminal techniques, where a flexible endoscope is accessed through a puncture into a vascular branch or through one end of the gastrointestinal tract (e.g., the mouth or the rectum). These flexible endoscopes may contain lumens for purposes of irrigation, suction or passage or surgical instruments (e.g., snares, organ catheters, biopsy devices, etc.).

Many other surgical procedures utilize endoscopic instruments which are often inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who attempt to find ways to make endoscopic instruments that fit through the smaller cannulas.

Many endoscopic surgical procedures require cutting or ligating blood vessels or vascular tissue. Due to the inherent spatial considerations and accessibility of the indoluminal sight, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue.

It is thought that the process of coagulating vessels is fundamentally different than electrosurgical vessel sealing. For the purposes herein, "coagulation" is defined as a process of desiccating tissue wherein the tissue cells are ruptured and dried. "Vessel sealing" or "tissue sealing" is defined as the process of liquefying the collagen in the tissue so that it reforms into a fused mass. Coagulation of small vessels is sufficient to permanently close them, while larger vessels need to be sealed to assure permanent closure.

In order to effectively seal larger vessels (or tissue) two predominant mechanical parameters are accurately controlled—the pressure applied to the vessel (tissue) and the gap distance between the electrodes—both of which are affected by the thickness of the sealed vessel. More particularly, accurate application of pressure is important to oppose the walls of the vessel; to reduce the tissue impedance to a low enough value that allows enough electrosurgical energy through the tissue; to overcome the forces of expansion during tissue heating; and to contribute to the end tissue thickness which is an indication of a good seal. It has been determined that a typical fused vessel wall is optimum between 0.001 and 0.006 inches. Below this range, the seal may shred or tear and above this range the lumens may not be properly or effectively sealed.

With respect to smaller vessels, the pressure applied to the tissue tends to become less relevant whereas the gap distance between the electrically conductive surfaces becomes more significant for effective sealing. In other words, the chances of the two electrically conductive surfaces touching during activation increases as vessels become smaller.

As mentioned above, in order to properly and effectively seal larger vessels or tissue, a greater closure force between opposing jaw members is required. It is known that a large closure force between the jaws typically requires a large moment about the pivot for each jaw. This presents a design challenge because the jaw members are typically affixed with pins which are positioned to have small moment arms with respect to the pivot of each jaw member. A large force, coupled with a small moment arm, is undesirable because the large forces may shear the pins. As a result, designers compensate for these large closure forces by either designing instruments with metal pins and/or by designing instruments which at least partially offload these closure forces to reduce the chances of mechanical failure. As can be appreciated, if metal pivot pins are employed, the metal pins should be insulated to avoid the pin acting as an alternate current path between the jaw members which may prove detrimental to effective sealing.

Increasing the closure forces between electrodes may have other undesirable effects, e.g., it may cause the opposing electrodes to come into close contact with one another which may result in a short circuit and a small closure force may cause pre-mature movement of the tissue during compression and prior to activation. As a result thereof, providing an instrument which consistently provides the appropriate closure force between opposing electrode within a preferred pressure range will enhance the chances of a successful seal. As can be appreciated, relying on a surgeon to manually provide the appropriate closure force within the appropriate range on a consistent basis would be difficult and the resultant effectiveness and quality of the seal may vary. Moreover, the overall success of creating an effective tissue seal is greatly reliant upon the user's expertise, vision, dexterity, and experience in judging the appropriate closure force to uniformly, consistently and effectively seal the vessel. In other words, the success of the seal would greatly depend upon the ultimate skill of the surgeon rather than the efficiency of the instrument.

It has been found that the pressure range for assuring a consistent and effective seal is between about 3 kg/cm2 to about 16 kg/cm2 and, desirably, within a working range of 7 kg/cm2 to 13 kg/cm2. Manufacturing an instrument which is capable of providing a closure pressure within this working range has been shown to be effective for sealing arteries, tissues and other vascular bundles.

Various force-actuating assemblies have been developed in the past for providing the appropriate closure forces to affect vessel sealing. For example, one such actuating assembly has been developed by Valleylab, Inc. of Boulder, Colo., a division of Tyco Healthcare LP, for use with Valleylab's vessel sealing and dividing instrument commonly sold under the trademark LIGASURE ATLAS®. This assembly includes a four-bar mechanical linkage, a spring and a drive assembly which cooperate to consistently provide and maintain tissue pressures within the above working ranges. The LIGASURE ATLAS® is presently designed to fit through a 10 mm cannula and includes a bi-lateral jaw closure mechanism which is activated by a foot switch. A trigger assembly extends a knife distally to separate the tissue along the tissue seal. A rotating mechanism is associated with distal end of the handle to allow a surgeon to selectively rotate the jaw members to facilitate grasping tissue. Co-pending U.S. application Ser. Nos. 10/179,863 and 10/116,944 and PCT Application Ser. Nos. PCT/US01/01890 and PCT/7201/11340 describe in detail the operating features of the LIGASURE ATLAS® and various methods relating thereto. The contents of all of these applications are hereby incorporated by reference herein.

Electrosurgical snares are used in endoscopic electrosurgical procedures of the removal of intestinal polyps and the like. Electrosurgical snares are predominantly monopolar, are used typically without any feedback to the electrosurgical generator, and typically lack control over the amount of cauterization of tissue. During a poly removal procedure, power applied to a stem of the polyp must be carried away through the wall of the underlying tissue (i.e., intestinal wall or other body lumen).

It would be desirous to develop an endoscopic vessel sealing instrument which reduces the overall amount of mechanical force necessary to close the jaw members and to clamp tissue therebetween. It would also be desirous for the instrument to provide a variable-ratio mechanical advantage for manipulating the jaw members and clamping tissue, such that, for example, the jaw members can be closed on tissue, easier, quicker and with less user force than previously envisioned to clamp the tissue.

Additionally, it would be desirous for the instrument to include a blade for cutting tissue following electrosurgical sealing.

Additionally, it would be desirous for the instrument to be a bipolar instrument capable of reducing or limiting the effect to tissue captured between the jaw members.

Additionally, one must consider the ability to manipulate the position of the surgical end effector. Controls are available to bend the flexible endoscope to position the view angle and the ports relative to the surgical target. It is then additionally desirable to manipulate the surgical effector within the view field of the endoscope. This may be accomplished by any number of means, such as, for example, pull wires, thermally active memory wire, or micro-machines.

SUMMARY

The present disclosure relates to flexible endoscopic bipolar electrosurgical forceps for sealing and/or cutting tissue.

According to an aspect of the present disclosure, an endoscopic forceps for vessel sealing is provided. The endoscopic forceps includes a housing; a shaft extending from the housing and including a distal end configured and adapted to support an end effector assembly; and an end effector assembly operatively supported on the distal end of the shaft.

The end effector assembly includes two jaw members movable from a first position in spaced relation relative to one another to at least a second position closer to one another for grasping tissue therebetween. Each of the jaw members is adapted to connect to an electrosurgical energy source such that the jaw members are capable of conducting energy through tissue held therebetween to affect a tissue seal. The end effector assembly further includes an outer sleeve translatably disposed about the shaft. The sleeve has a first position in which the sleeve does not cover the jaw members, and a plurality of second positions in which the sleeve covers at least a portion of the two jaws to approximate the jaws at least partially toward one another. The end effector assembly includes a linkage operatively connected to at least one of the jaw members for pivoting both jaw members about a common pivot axis.

The endoscopic forceps includes a movable handle operatively associated with the housing. Accordingly, actuation of the movable handle relative to the housing results in movement of the outer sleeve relative the jaw members to actuate the end effector assembly between the first and second positions.

The jaw members may be biased to the first position. The jaw members are either unilateral or bilateral. The end effector assembly includes at least one stop member disposed on an inner facing surface of at least one of the jaw members. The end effector assembly may deliver a working pressure of about 3 kg/cm$^2$ to about 16 kg/cm$^2$, preferably of about 7 kg/cm$^2$ to about 13 kg/cm$^2$.

In an embodiment, the jaw members are pivotable to a substantially orthogonal orientation relative to a longitudinal axis of the shaft. The linkage desirably actuates the jaw members from the first position to a second position. The linkage may be operatively connected to one of the jaw members.

The shaft and outer sleeve may be at least partially flexible.

According to another aspect of the present disclosure, the endoscopic forceps includes a housing; a shaft extending from the housing and including a distal end configured and adapted to support an end effector assembly; and an end effector assembly operatively supported on the distal end of the shaft. The end effector assembly includes two jaw members movable from a first position in spaced relation relative to one another to at least a second position closer to one another for grasping tissue therebetween. Each of the jaw members is adapted to connect to an electrosurgical energy source such that the jaw members are capable of conducting energy through tissue held therebetween to affect a tissue seal. The jaw members are biased to the first position. The end effector assembly of the endoscopic forceps further includes a wire having a proximal end connectable to an electrosurgical energy source and a distal end translatably extending out of one of the jaw members and operatively associated with the other of the jaw members. Accordingly, in use, withdrawal of the proximal end of the wire results in movement of the jaw members from the first position to a second position and cinching of the wire onto and/or around the tissue.

The jaw members may be unilateral or bilateral.

The distal end of the wire may translatably extend through the other of the jaw members and may be secured to itself. The wire may be fabricated from shape-memory alloys.

It is envisioned that at least a portion of the shaft is flexible. In an embodiment, a distal most end of the shaft is rigid.

The end effector assembly may further include a scissor blade operatively supported on a distal end of the shaft and movable from a first position in which the scissor blade is substantially aligned with one of said jaw members and a plurality of second positions in which the scissor blade is out of alignment with the one jaw member and extends across to the other of the jaw members thereby severing tissue grasped between the jaw members.

In an embodiment, the end effector assembly may still further include a scissor blade linkage operatively connected to the scissor blade. Accordingly, in use, movement of the scissor linkage results in actuation of the scissor blade between the first position and any number of second positions.

According to still a further aspect of the present disclosure, the endoscopic forceps includes a housing; a shaft extending from the housing and including a distal end configured and adapted to support an end effector assembly; and an end effector assembly operatively supported on the distal end of the shaft. The end effector assembly includes a cutting blade supported on the distal end of the shaft, the cutting blade including a cutting edge extending in a distal direction; a movable jaw member translatably supported on the shaft, the movable jaw member including a tissue contacting portion extending across a longitudinal axis of the shaft; and an anvil member slidably supported on the movable jaw member between the tissue contacting portion of the movable jaw member and the cutting blade, the anvil member defining a blade slot formed therein for selectively receiving the cutting blade therethrough. The endoscopic forceps further includes a movable handle operatively associated with the housing, wherein actuation of the movable handle relative to the housing results in movement of the movable jaw member relative to the shaft.

The end effector assembly may further include a biasing member disposed between the anvil member and the cutting blade for maintaining the anvil member biased a distance away from the cutting blade such that the cutting blade does not extend through the anvil member.

The end effector assembly may include a first position wherein the tissue contacting portion of the movable jaw member is spaced a distance from the anvil member for receiving a target tissue therein, and the anvil member is spaced a distance from the cutting blade such that the cutting blade does not extend through the blade slot formed therein. The end effector assembly may further include a second position wherein the tissue contacting portion of the movable jaw member is approximated toward the anvil member to grasp the tissue therebetween, and the anvil member is spaced a distance from the cutting blade such that the cutting blade does not extend through the blade slot formed therein. The end effector assembly may include a third position wherein the tissue contacting portion of the movable jaw member is approximated toward the anvil member to grasp the tissue therebetween, and the anvil member is approximated toward the cutting blade such that the cutting edge of the cutting blade extends through the blade slot formed therein severs the tissue extending thereacross.

For a better understanding of the present disclosure and to show how it may be carried into effect, reference will now be made by way of example to the accompanying drawings.

BRIEF DESCRIPTION OF THE DRAWINGS

Various embodiments of the subject instrument are described herein with reference to the drawings wherein.

DETAILED DESCRIPTION

Figure 1:
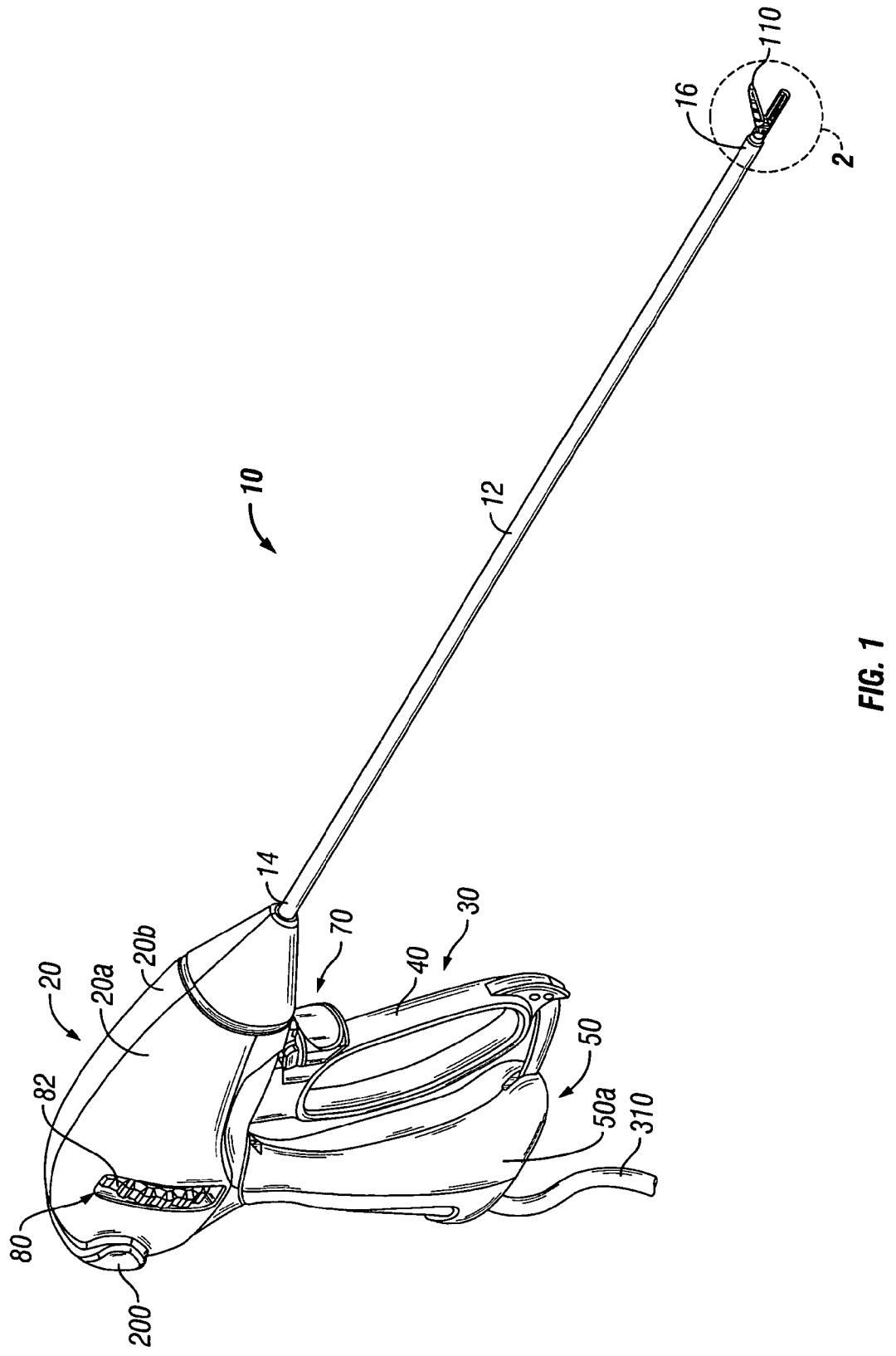
FIG. 1 is a perspective view of an endoscopic bipolar forceps showing a housing, a shaft and an end effector assembly according to the present disclosure.
Figure 2:
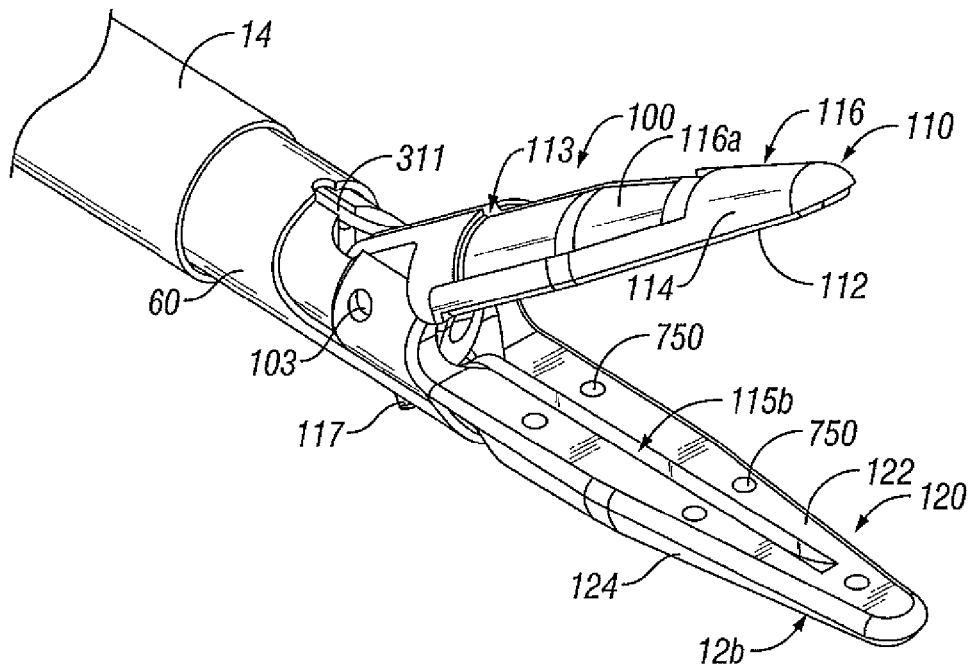
FIG. 2 is an enlarged perspective view of the end effector assembly of FIG. 1, with the jaw members in an open configuration.

Turning now to FIGS. 1 and 2, an embodiment of an endoscopic bipolar forceps 10 is shown for use with various surgical procedures and generally includes a housing 20, a handle assembly 30, a rotating assembly 80, a trigger assembly 70 and an end effector assembly 100 that operates to grasp, seal, divide, cut and dissect corporal tissue and the like. Although the majority of the figure drawings depict a bipolar forceps 10 for use in connection with endoscopic surgical procedures, the present disclosure may be used for more traditional open surgical procedures. For the purposes herein, the forceps 10 is described in terms of an endoscopic instrument, however, it is contemplated that an open version of the forceps may also include the same or similar operating components and features as described below.

In the drawings and in the descriptions that follow, the term "proximal," as is traditional, will refer to the end of the forceps 10 which is closer to the user, while the term "distal" will refer to the end that is farther from the user.

Forceps 10 includes a shaft 12 that has a distal end 16 dimensioned to mechanically engage end effector assembly 100 and a proximal end 14 that mechanically engages the housing 20. Proximal end 14 of shaft 12 is received within housing 20 and appropriate mechanical and electrical connections relating thereto are established.

As best seen in FIG. 1, forceps 10 also includes an electrosurgical cable 310 that connects the forceps 10 to a source of electrosurgical energy, e.g., a generator (not shown). It is contemplated that generators such as those sold by Valleylab—a division of Tyco Healthcare LP, located in Boulder Colo. are used as a source of electrosurgical energy, e.g., FORCE EZ™ Electrosurgical Generator, FORCE FX™ Electrosurgical Generator, FORCE 1C™, FORCE 2™ Generator, SurgiStat™ II. One such system is described in commonly-owned U.S. Pat. No. 6,033,399 entitled "ELECTROSURGICAL GENERATOR WITH ADAPTIVE POWER CONTROL" the entire contents of which are hereby incorporated by reference herein. Other systems have been described in commonly-owned U.S. Pat. No. 6,187,003 entitled "BIPOLAR ELECTROSURGICAL INSTRUMENT FOR SEALING VESSELS" the entire contents of which are also incorporated by reference herein.

In one embodiment, the generator includes various safety and performance features including isolated output, independent activation of accessories. It is envisioned that the electrosurgical generator includes Valleylab's Instant Response™ technology features that provides an advanced feedback system to sense changes in tissue 200 times per second and adjust voltage and current to maintain appropriate power. The Instant Response™ technology is believed to provide one or more of the following benefits to surgical procedure:

Consistent clinical effect through all tissue types;

Reduced thermal spread and risk of collateral tissue damage;

Less need to "turn up the generator"; and

Designed for the minimally invasive environment.

Cable 310 is internally divided into several cable leads (not shown) which each transmit electrosurgical energy through their respective feed paths through the forceps 10 to the end effector assembly 100.

Handle assembly 30 includes a fixed handle 50 and a movable handle 40. Fixed handle 50 is integrally associated with housing 20 and handle 40 is movable relative to fixed handle 50. In one embodiment, rotating assembly 80 is integrally associated with housing 20 and is rotatable approximately 180 degrees about a longitudinal axis.

As mentioned above, end effector assembly 100 is attached at distal end 16 of shaft 12 and includes a pair of opposing jaw members 110 and 120. Movable handle 40 of handle assembly 30 is ultimately connected to a drive assembly (not shown) which, together, mechanically cooperate to impart movement of jaw members 110 and 120 from an open position wherein jaw members 110 and 120 are disposed in spaced relation relative to one another, to a clamping or closed position wherein jaw members 110 and 120 cooperate to grasp tissue therebetween.

It is envisioned that forceps 10 may be designed such that it is fully or partially disposable depending upon a particular purpose or to achieve a particular result. For example, end effector assembly 100 may be selectively and releasably engageable with distal end 16 of the shaft 12 and/or the proximal end 14 of shaft 12 may be selectively and releasably engageable with the housing 20 and the handle assembly 30. In either of these two instances, the forceps 10 would be considered "partially disposable" or "reposable", i.e., a new or different end effector assembly 100 (or end effector assembly 100 and shaft 12) selectively replaces the old end effector assembly 100 as needed. As can be appreciated, the presently disclosed electrical connections would have to be altered to modify the instrument to a reposable forceps.

As shown best in FIG. 2, end effector assembly 100 includes opposing jaw members 110 and 120 that cooperate to effectively grasp tissue for operative purposes. End effector assembly 100 may be designed as a unilateral assembly, i.e., jaw member 120 is fixed relative to the shaft 12 and jaw member 110 pivots about a pivot pin 103 to grasp tissue and the like or as a bilateral assembly, i.e., both jaw members pivot relative to one another.

More particularly, and with respect to the particular embodiments shown in FIG. 2, the unilateral end effector assembly 100 includes one stationary or fixed jaw member 120 mounted in fixed relation to shaft 12 and pivoting jaw member 110 mounted about a pivot pin 103 attached to the stationary jaw member 120. A reciprocating sleeve 60 is slidingly disposed within the shaft 12 and is remotely operable by a drive assembly. The pivoting jaw member 110 includes a detent or protrusion 117 that extends from jaw member 110 through an aperture (not shown) disposed within the reciprocating sleeve 60. Pivoting jaw member 110 is actuated by sliding the sleeve 60 axially within shaft 12 such that a distal end of the aperture abuts against detent 117 on pivoting jaw member 110. Pulling sleeve 60 proximally closes jaw members 110 and 120 about tissue and the like, and pushing sleeve 60 distally opens jaw members 110 and 120.

As illustrated in FIG. 2, a knife channel 115b runs through the center of the jaw member 120 (a complementary knife channel is formed in jaw member 110) such that a blade from a knife assembly (not shown) may cut through the tissue grasped between jaw members 110 and 120 when jaw members 110 and 120 are in a closed position. Details relating to the knife channel 115 and the knife actuating assembly including trigger assembly 70 are explained in limited detail herein and explained in more detail with respect to commonly-owned U.S. patent application Ser. No. 10/460,926, filed Jun. 13, 2003 and Ser. No. 10/953,757, filed Sep. 29, 2004, the entire contents of which are both incorporated by reference herein.

With continued reference to FIG. 2, jaw member 110 also includes a jaw housing 116 having an insulative substrate or insulator 114 and an electrically conducive sealing surface 112. In one embodiment, insulator 114 is dimensioned to securely engage the electrically conductive sealing surface 112. This may be accomplished by stamping, by overmolding, by overmolding a stamped electrically conductive sealing plate and/or by overmolding a metal injection molded seal plate. Movable jaw member 110 also includes a wire channel 113 designed to guide a cable lead 311 into electrical continuity with electrically conducive sealing surface 112 as described in more detail below.

Desirably, jaw member 110 has an electrically conducive sealing surface 112 which is substantially surrounded by an insulating substrate 114. Insulating substrate 114, electrically conductive sealing surface 112 and the outer, non-conductive jaw housing 116 can be dimensioned to limit and/or reduce many of the known undesirable effects related to tissue sealing, e.g., flashover, thermal spread and stray current dissipation. Alternatively, it is envisioned that jaw members 110 and 120 may be manufactured from a ceramic-like material and the electrically conducive sealing surface(s) 112 thereof may be coated onto the ceramic-like jaw members 110 and 120.

It is envisioned that the electrically conductive sealing surface 112 may also include an outer peripheral edge that has a pre-defined radius and the insulating substrate 114 meets the electrically conductive sealing surface 112 along an adjoining edge of the sealing surface 112 in a generally tangential position. In one embodiment, at the interface, the electrically conducive sealing surface 112 is raised relative to the insulating substrate 114. These and other envisioned embodiments are discussed in co-pending, commonly assigned application Ser. No. PCT/US01/11412 entitled "ELECTROSURGICAL INSTRUMENT WHICH REDUCES COLLATERAL DAMAGE TO ADJACENT TISSUE" by Johnson et al. and co-pending, commonly assigned application Ser. No. PCT/US01/11411 entitled "ELECTROSURGICAL INSTRUMENT WHICH IS DESIGNED TO REDUCE THE INCIDENCE OF FLASHOVER" by Johnson et al.

In one embodiment, the electrically conducive sealing surface 112 and the insulating substrate 114, when assembled, form a longitudinally-oriented slot (not shown) defined therethrough for reciprocation of the knife blade. It is envisioned that knife channel (not shown) of jaw member 110 cooperates with a corresponding knife channel 115b defined in stationary jaw member 120 to facilitate longitudinal extension of the knife blade along a preferred cutting plane to effectively and accurately separate the tissue.

Jaw member 120 includes similar elements to jaw member 110 such as a jaw housing having an insulating substrate 124 and an electrically conductive sealing surface 122 which is dimensioned to securely engage the insulating substrate 124. Likewise, the electrically conductive surface 122 and the insulating substrate 124, when assembled, include a longitudinally-oriented channel 115a defined therethrough for reciprocation of the knife blade. As mentioned above, when the jaw members 110 and 120 are closed about tissue, the knife channels of jaw members 110, 120 form a complete knife channel to allow longitudinal extension of the knife blade in a distal fashion to sever tissue. It is also envisioned that the knife channel may be completely disposed in one of the two jaw members, e.g., jaw member 120, depending upon a particular purpose.

As best seen in FIG. 2, jaw member 120 includes a series of stop members 750 disposed on the inner facing surfaces of the electrically conductive sealing surface 122 to facilitate gripping and manipulation of tissue and to define a gap between opposing jaw members 110 and 120 during sealing and cutting of tissue. It is envisioned that the series of stop members 750 may be employed on one or both jaw members 110 and 120 depending upon a particular purpose or to achieve a desired result. A detailed discussion of these and other envisioned stop members 750 as well as various manufacturing and assembling processes for attaching and/or affixing the stop members 750 to the electrically conductive sealing surfaces 112, 122 are described in commonly-assigned, co-pending U.S. application Ser. No. PCT/US01/11413 entitled "VESSEL SEALER AND DIVIDER WITH NON-CONDUCTIVE STOP MEMBERS" by Dycus et al. which is hereby incorporated by reference in its entirety herein.

Jaw members 110 and/or 120 may be designed to be fixed to the end of a tube 60 (see FIG. 2) extending from handle assembly 30 and configured for rotation about a longitudinal axis thereof. In this manner, rotation of tube 60 may impart rotation to jaw members 110 and/or 120 of end effector assembly 100.

Figure 3:
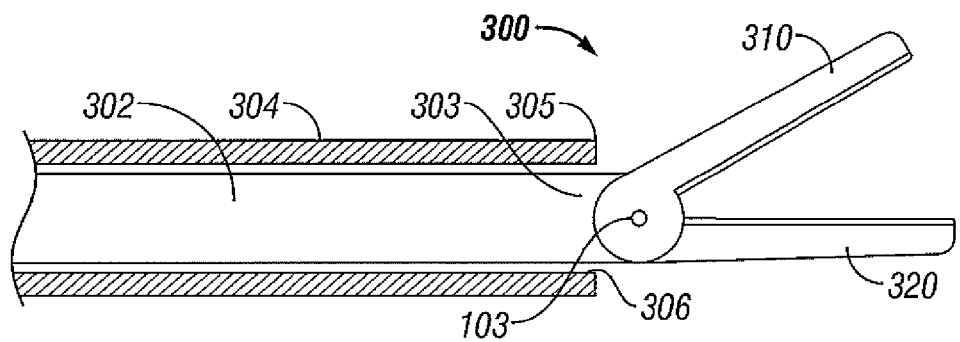
FIG. 3 is a schematic, side elevational view of an end effector according to an embodiment of the present disclosure, with the jaw members in an open configuration.
Figure 4:
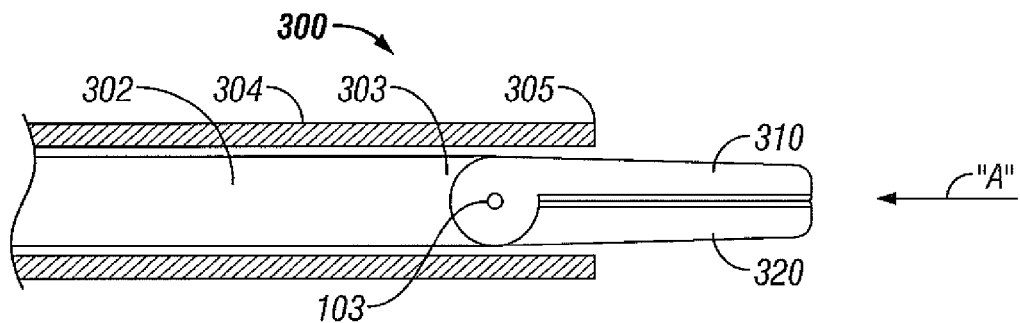
FIG. 4 is a schematic, side elevational view of the end effector of FIG. 3 with the jaw members in a closed configuration.

Turning now to FIGS. 3 and 4, an alternate embodiment of end effector assembly 300, in accordance with the present disclosure, is shown and will be described. It is envisioned that end effector assembly 300 may include some, if not all, of the features and elements provided and/or associated with end effector assembly 100.

As seen in FIGS. 3 and 4, end effector assembly 300 includes a central shaft 302 supporting a pair of jaws 310, 320 at a distal end thereof in a unilateral arrangement. End effector assembly 300 includes a first or fixed jaw member 320 supported on a distal end 303 of central shaft 302, and a second or movable jaw member 310 pivotably supported at distal end 303 of central shaft 302 by a pivot pin 103. First and second jaw members 320, 310 are in juxtaposed relation to one another and are movable between an open condition, wherein tissue may be positioned between jaw members 320, 310, and a closed configuration, wherein jaw members 320, 310 grasp and/or clamp onto tissue. Jaw members 320, 310 are biased to the open condition by a biasing member, e.g., spring, or the like (not shown).

End effector assembly 300 further includes an outer catheter sleeve 304 defining a front or distal edge 305 and a lumen 306 therethrough. Lumen 306 of outer sleeve 304 is configured and dimensioned to translatably receive central shaft 302 and jaw members 320, 310 therein.

In operation, as central shaft 302 is withdrawn into outer sleeve 304, as indicated by arrow "A" in FIG. 4, distal edge 305 of outer sleeve 304 abuts against movable jaw member 310 and forces movable jaw member 310 towards fixed jaw member 320. In so doing, tissue disposed between jaw members 310, 320 is clamped or grasped therebetween. It is understood that, in certain embodiments, that the greater the degree of withdrawal of central shaft 302 and jaw member 310, 320 into lumen 306 of outer sleeve 304, the greater the clamping force exerted on the tissue disposed between jaw members 310, 320.

It is envisioned and within the scope of the present disclosure for central shaft 302 and/or outer sleeve 304 to be fabricated from a flexible material or the like. Central shaft 302 and/or outer sleeve 304 may be fabricated from any one of or a combination of materials including and not limited to, NITINOL (e.g., nickel-titanium alloys), polyurethane, polyester, and/or polymethylsiloxane material (PDMS), fluorinated ethylene-propylene (FEP), polytetrafluoroethylene (PTFE), nylon, etc.

Figure 5:
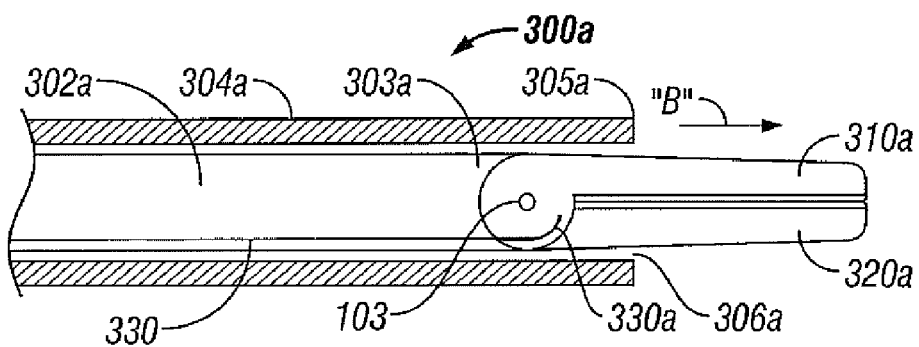
FIG. 5 is a schematic, side elevational view of an end effector according to another embodiment of the present disclosure, in a first closed configuration.
Figure 6:
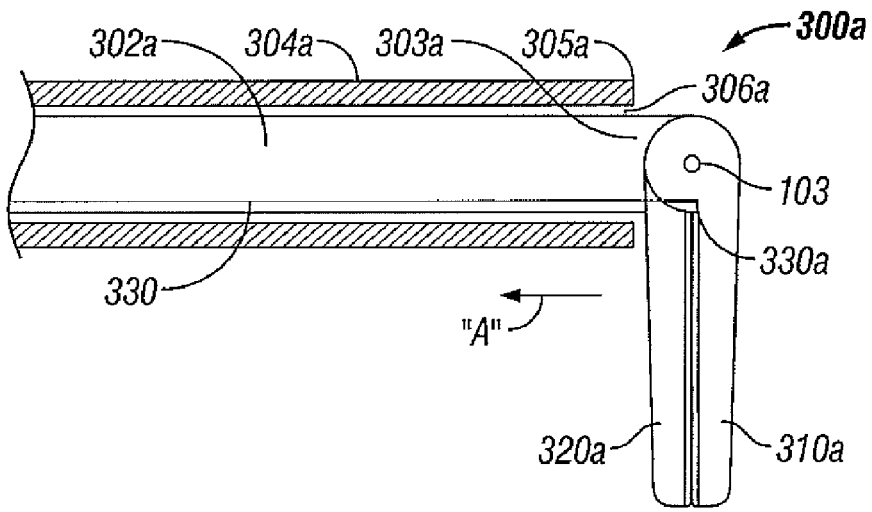
FIG. 6 is a schematic, side elevational view of the end effector of FIG. 5, in a second closed configuration for transmitting clamping force to tissue interposed therebetween.

Turning now to FIGS. 5 and 6, an end effector assembly, according to another embodiment of the present disclosure, is generally designated as 300a. It is envisioned that end effector assembly 300b may include some, if not all, of the features and elements provided and/or associated with end effector assembly 100.

End effector assembly 300a includes a pair of jaw members 310a, 320a each pivotably supported at a distal end 303a of a central shaft 302a via a pivot pin 103. End effector assembly 300a further includes an outer catheter sleeve 304a defining a lumen 306a therethrough. Lumen 306a of outer sleeve 304a is configured and dimensioned to translatably receive central shaft 302a and jaw members 310a, 320a therein.

As seen in FIGS. 5 and 6, a linkage 330 or the like may be provided for actuating one of jaw members 310a, 320a relative to the other thereby effectuating opening and closing of end effector assembly 300a. A distal end 330a of linkage 330 is desirably connected to second jaw member 310a at a location distal of pivot pin 103 when jaw members 310a, 320a are disposed within outer sleeve 304a. Linkage 330 is desirably operatively connected to second jaw member 310a in such a manner so as to effectuate rotation of second jaw member 310a toward first jaw member 320a upon movement of linkage 330 in a proximal direction.

In use, with jaw members 310a, 320a in a closed condition, jaw members 310a, 320a are advanced through lumen 306a of outer sleeve 304, as indicated by arrow "B" of FIG. 5. After jaw members 310a, 320a have cleared the distal end or edge 305a of outer sleeve 304a (i.e., pivot pin 103 has cleared or advanced beyond the distal end or edge 305a of outer sleeve 304a), jaw members 310a, 320a may both be pivoted about pivot pin 103 to a substantially orthogonal orientation relative to central shaft 302a, as seen in FIG. 6. In order to pivot or rotate jaw members 310a, 320a about pivot pin 103, linkage 330 is moved in a proximal direction, as indicated by arrow "A".

With jaw members 310a, 320a oriented in an orthogonal direction, jaw members 310a, 320a may be opened and closed by moving linkage 330 in a distal or proximal direction. For example, by moving linkage 330 in a distal direction, second jaw member 310a is rotated about pivot pin 103 thereby spacing second jaw member 310a from first jaw member 320a. In so doing, end effector assembly 300a is configured to an open condition and the tissue contacting surface of first jaw member 320a is oriented approximately 90° relative to a longitudinal axis of outer sleeve 304a. With end effector assembly 300a in an open condition, tissue may be placed between jaw members 310a, 320a or jaw members 310a, 320a may be placed over the tissue.

Following placement of tissue between jaw members 310a, 320a, linkage 330 may be moved in a proximal direction thereby rotating second jaw member 310a about pivot pin 103 to approximate second jaw member 310a toward first jaw member 320a. In so doing, end effector assembly 300a is moved to a closed condition to grasp the tissue interposed between first and second jaw members 320a, 310a. Since jaw members 310b, 320b are in an orthogonal configuration, retraction of linkage 330 in a proximal direction results in application of the clamping force in a substantially linear direction relative to central shaft 302b.

Following treatment of the tissue, linkage 330 may be reactuated to release the treated tissue from between first and second jaw members 320a, 310a. With the treated tissue released from between first and second jaw members 320a, 310a, central shaft 302a is withdrawn through outer sleeve 304a. In so doing, first and second jaw members 320a, 310a are re-oriented to an axially aligned orientation due to a camming action between the distal edge of outer sleeve 304a and first jaw member 320a.

It is envisioned and within the scope of the present disclosure for central shaft 302a and/or outer sleeve 304a to be fabricated from a flexible material or the like.

Figure 7:
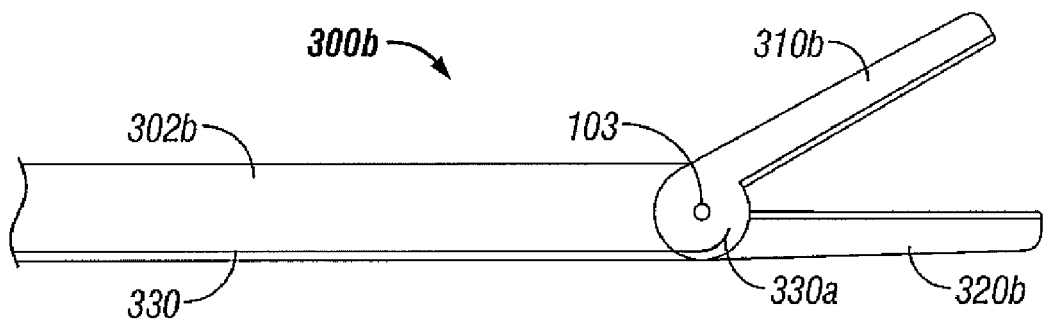
FIG. 7 is a schematic, side elevational view of an end effector according to yet another embodiment of the present disclosure, with the jaw members in an open configuration.
Figure 8:
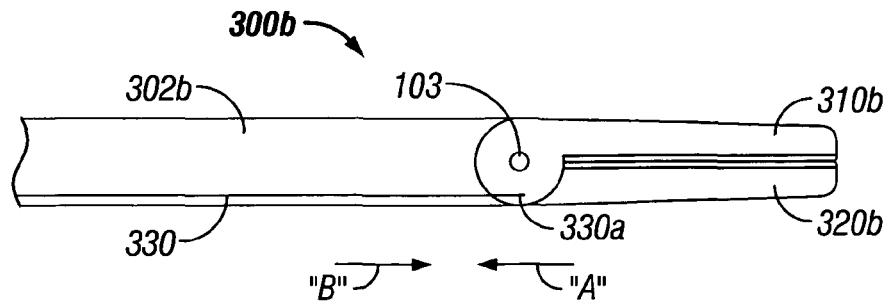
FIG. 8 is a schematic, side elevational view of the end effector of FIG. 7 with the jaw members in a closed configuration.

Turning now to FIGS. 7 and 8, an end effector assembly, according to an alternate embodiment of the present disclosure, is generally shown as 300b. It is envisioned that end effector assembly 300b may include some, if not all, of the features and elements provided and/or associated with end effector assembly 100.

As seen in FIGS. 7 and 8, end effector assembly 300b includes a central shaft 302b supporting a pair of jaws 310b, 320b at a distal end thereof in a unilateral arrangement. End effector assembly 300b includes a first or fixed jaw member 320b supported on a distal end of central shaft 302b, and a second or movable jaw member 310b pivotably supported at distal end of central shaft 302b by a pivot pin 103. First and second jaw members 320b, 310b are in juxtaposed relation to one another and are movable between an open condition, wherein tissue may be positioned between jaw members 320b, 310b, and a closed configuration, wherein jaw members 320b, 310b grasp and/or clamp onto tissue.

As seen in FIGS. 7 and 8, a linkage 330b or the like may be provided for actuating second jaw member 310b relative to first jaw member 320b. A distal end 330a of linkage 330 is desirably connected to second jaw member 310. In particular, as seen in FIG. 7, distal end 330a of linkage 330 is connected to second jaw member 310a in such a manner so as to effectuate rotation of second jaw member 310b toward first jaw member 320b upon movement of linkage 330 in a proximal direction, as indicated by arrow "A", or away from first jaw member 320b upon movement of linkage 330 in a distal direction, as indicated by arrow "B".

As disclosed above, it is envisioned and within the scope of the present disclosure that central shaft 302b may be fabricated from a flexible material or the like.

Figure 9:
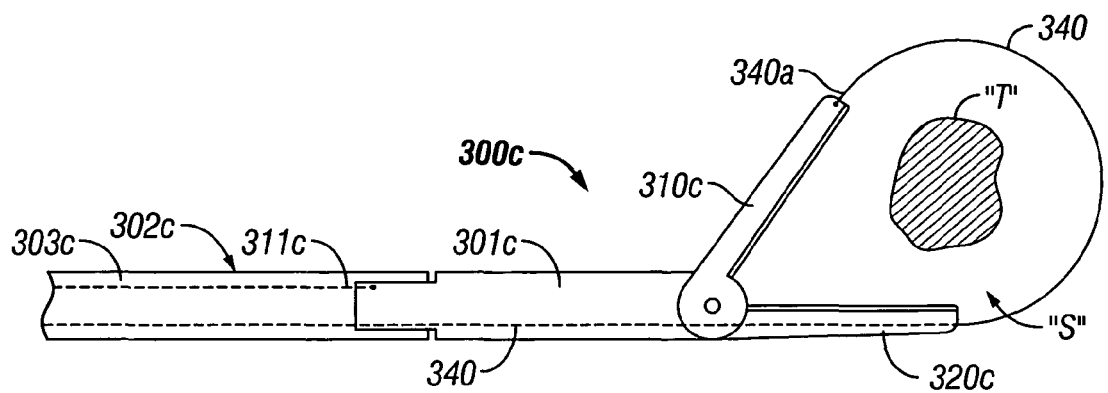
FIG. 9 is a schematic, side elevational view of an end effector according to still another embodiment of the present disclosure, with the jaw members in an open configuration.
Figure 10:
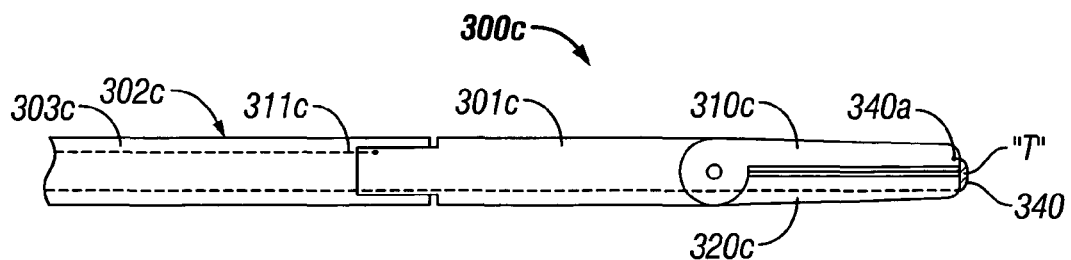
FIG. 10 is a schematic, side elevational view of the end effector of FIG. 9 with the jaw members in a closed configuration.

Turning now to FIGS. 9 and 10, an end effector assembly, according to a further embodiment of the present disclosure, is generally designated as 300c. End effector assembly 300c is substantially identical to end effector assembly 300b and will only be discussed in detail to the extent necessary to identify differences in construction and operation.

As seen in FIGS. 9 and 10, a central body portion 302c of end effector assembly 300c includes a rigid distal portion 301c and a flexible proximal portion 303c. Jaw members 310c, 320c are arranged in a unilateral configuration and are actuatable by any of the methods described above or known by one having skill in the art. Jaw members 310c, 320c are desirably biased to an open condition by a biasing member, e.g., spring, or the like (not shown), or by the wire snare 340.

As seen in FIGS. 9 and 10, end effector assembly 300c includes a wire snare 340 extending out of one of jaw members 310c, 320c and anchored to the other of jaw members 310c, 320c. In particular, wire snare 340 is disposed within central body portion 302c and includes a proximal end (not shown) which connects to an electrosurgical energy source, and a distal end 340a that extends out through fixed jaw member 320c and attaches to a distal end or tip of movable jaw member 310c.

It is envisioned that wire 340 may be fabricated from a shape memory alloy, such as, for example, NITINOL, or the like. Accordingly, as seen in FIG. 9, when end effector assembly 300c is in the open condition, wire 340 has a substantially arcuate shape or configuration.

In use, in order to close end effector assembly 300c, wire 340 is withdrawn in a proximal direction thereby approximating the distal tip of movable jaw member 310c toward the distal tip of fixed jaw member 320c. In so doing jaw members 310c, 320c are approximated toward one another and desirably clamp onto tissue "T".

In one mode of operation, with end effector assembly 300c in an open condition and with wire 340 in an expanded condition, as seen in FIG. 9, end effector assembly 300c is placed over tissue "T" to be excised, e.g., a polyp or the like, such that tissue "T" is interposed and/or disposed within the space or area "S" defined between jaw members 310c, 320c and wire 340. With tissue "T" positioned in space "S", the proximal end of wire 340 is drawn in a proximal direction thereby closing end effector assembly 300c (e.g., approximating jaw members 310c, 320c) onto tissue "T" and cinching wire 340 about tissue "T".

Wire 340 is withdrawn an amount sufficient to tightly close end effector assembly 300c onto and/or about tissue "T" and to apply pressure to tissue "T" between the jaw members 310c, 320c. At such a time, electrical current or electrical energy is transmitted through wire 340 and/or to the electrically conducive sealing surface(s) of jaw members 310c, 320c. The electrical current or energy is transmitted at a level and for a time sufficient to heat wire 340 to cut through tissue "T" and remove tissue "T" from the underlying or remaining tissue.

It is envisioned that wire 340 may or may not be insulated. Additionally, distal portion 301c of central shaft 300c may be fabricated from a rigid, electrically conductive material. In so doing, an electrical lead 311c may extend through flexible proximal portion 303c of central shaft 302c and electrically connect to a proximal end of rigid portion 301c.

In another mode of operation, with end effector assembly 300c in an open condition and with wire 340 in an expanded condition, end effector assembly 300c is placed over tissue "T" to be excised, e.g., a polyp or the like, such that tissue "T" is interposed and/or disposed between jaw members 310c, 320c. With tissue "T" so positioned, the proximal end of wire 340 is drawn in a proximal direction thereby cinching wire 340 and closing end effector assembly 300c (e.g., approximating jaw members 310c, 320c) onto tissue "T".

Wire 340 is withdrawn an amount sufficient to tightly close end effector assembly 300c onto tissue "T" and to apply pressure to tissue "T" between the jaw members 310c, 320c. It is envisioned that in the current mode of operation, further withdrawal of wire 340 may result in pivoting of end effector assembly 300c about pivot pin 103 to improve the visibility at the surgical site.

Figure 11:
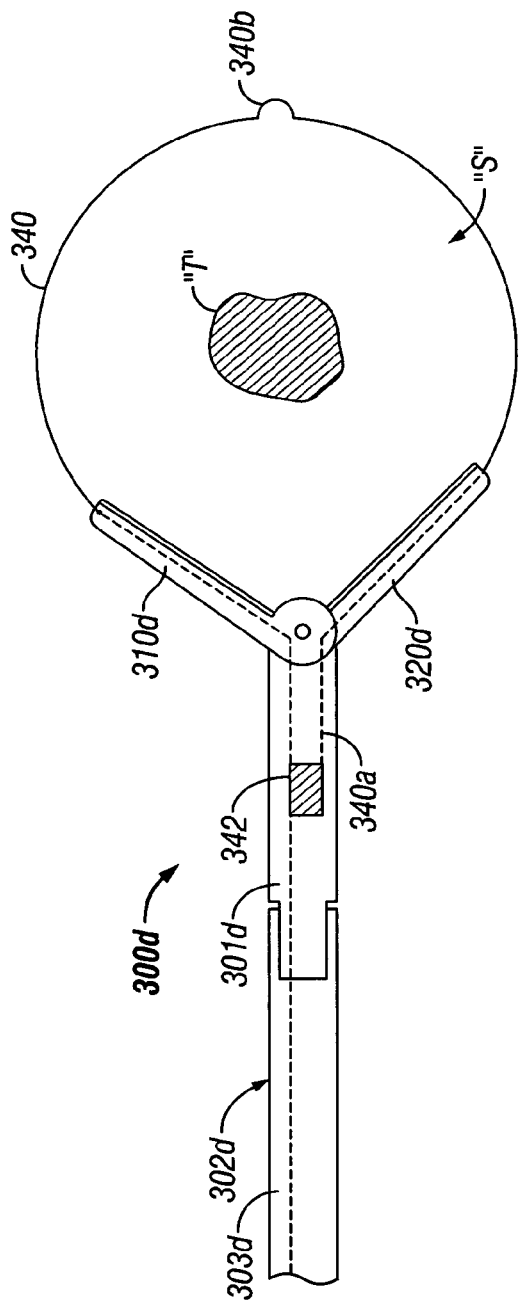
FIG. 11 is a schematic, side elevational view of an end effector according to another embodiment of the present disclosure, with the jaw members in an open configuration.
Figure 12:
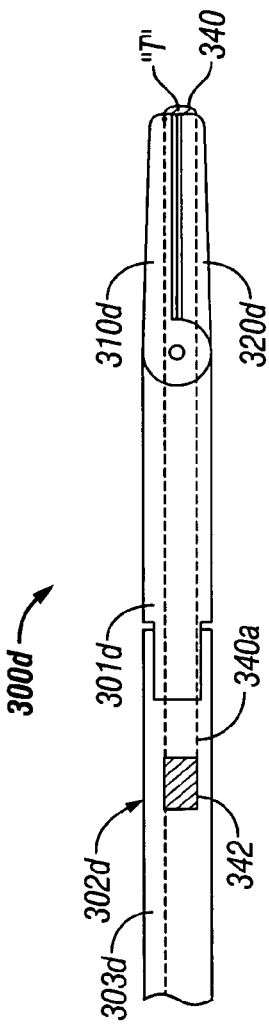
FIG. 12 is a schematic, side elevational view of the end effector of FIG. 11 with the jaw members in a closed configuration.

Turning now to FIGS. 11 and 12, an end effector assembly, according to a further embodiment of the present disclosure, is generally designated as 300d. End effector assembly 300d is substantially identical to end effector assembly 300c and will only be discussed in detail to the extent necessary to identify differences in construction and operation.

As seen in FIGS. 11 and 12, end effector assembly 300d includes a wire 340 extending out of one of jaw members 310d, 320d and into the other of jaw members 310d, 320d. In particular, wire 340 is disposed within central body portion 302d and includes a proximal end (not shown) which connects to an electrosurgical energy source, and a distal end 340a which extends out through a distal tip of first jaw member 320d and back into a distal tip of second jaw member 310d. Distal end 340a of wire 340 is anchored or secured to itself according to any known method, including and not limited to use of a junction block 342. In this manner, as will be described in greater detail below, withdrawal of wire 340 in a proximal direction results in withdrawal of wire 340 through both jaw members 310b, and 320d.

While end effector assembly 300d is shown as having bilateral jaw member arrangement, it is envisioned and within the scope of the present disclosure for end effector assembly 300d to have a unilateral jaw member arrangement. It is envisioned that when end effector assembly 300d is in the open condition, wire 340 has a substantially arcuate shape or configuration. Wire 340 includes a nipple region 340b formed along a length thereof. In use, when cinching wire 340 it is desired for tissue "T" to be positioned within nipple region 340b of wire 340.

In use, in order to close end effector assembly 300d, wire 340 is withdrawn in a proximal direction, by pulling on the proximal end of wire 340, thereby approximating the distal tips of jaw members 310d, 320d toward one another. Since distal end 340a of wire 340 is secured to itself by junction block 342, by pulling on the proximal end of wire 340, distal end 340a of wire 340 is drawn into both jaw members 310d, 320d substantially equally.

In operation, with end effector assembly 300d in an open condition and with wire 340 in an expanded condition, as seen in FIG. 11, end effector assembly 300d is placed over tissue "T" to be excised, e.g., a polyp or the like, such that tissue "T" is interposed and/or disposed within the space or area "S" defined between jaw members 310d, 320d and wire 340. With tissue "T" positioned in space "S", the proximal end of wire 340 is drawn in a proximal direction thereby closing end effector assembly 300d (e.g., approximating jaw members 310d, 320d simultaneously) onto tissue "T" and cinching wire 340 about tissue "T".

Wire 340 is withdrawn an amount sufficient to tightly close end effector assembly 300d onto and/or about tissue "T" and to apply pressure to tissue "T" between jaw members 310d, 320d. At such a time, electrical current or electrical energy is transmitted through wire 340 and/or to the electrically conducive sealing surface(s) of jaw members 310d, 320d. The electrical current or energy is transmitted at a level and for a time sufficient to heat wire 340 to cut through tissue "T" and remove tissue "T" from the underlying or remaining tissue.

In accordance with the present disclosure, the rigid nature of jaw members 310, 320 provides greater support and/or control of wire 340 as compared to conventional wire snare instruments and the like.

Turning now to FIGS. 13-17, an end effector assembly, according to a further embodiment of the present disclosure, is generally designated as 300e. End effector assembly 300e is substantially identical to end effector assembly 300c and will only be discussed in detail to the extent necessary to identify differences in construction and operation.

End effector assembly 300e further includes a knife or scissor blade 350 pivotably connected to a distal end of central shaft 302e. Scissor blade 350 may be pivotably connected to the distal end of central shaft 302e via pivot pin 103. Scissor blade 350 defines a cutting edge 350a or the like.

As seen in FIGS. 13-17, a linkage 352 or the like may be provided for actuating scissor blade 350 relative to jaw members 310e, 320e of end effector assembly 300e to sever tissue "T" and the like. A distal end 352a of linkage 352 is desirably connected to scissor blade 352 at a location desirably distal of pivot pin 103. Linkage 352 is desirably operatively connected to scissor blade 350 in such a manner so as to effectuate rotation of scissor blade 350 upon movement of linkage 352 in a proximal direction.

Figure 13:
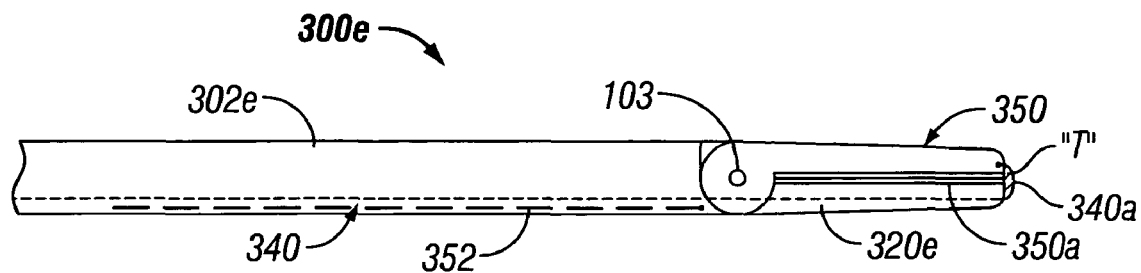
FIG. 13 is a schematic, side elevational view of an end effector according to yet another embodiment of the present disclosure, illustrating a scissor blade in an unactuated condition.
Figure 14:
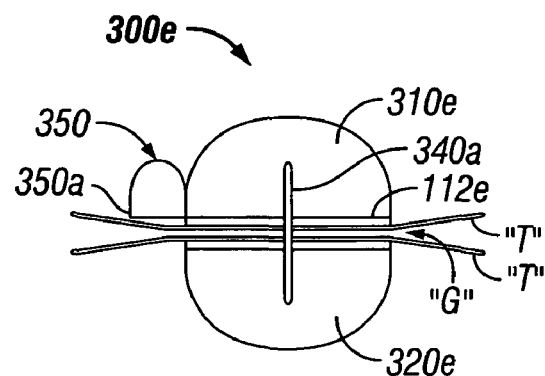
FIG. 14 is a schematic, distal end view of the end effector of FIG. 13, including tissue interposed between the jaw members.
Figure 15:
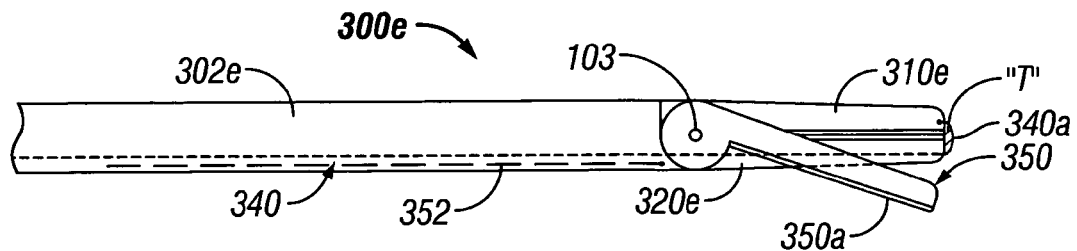
FIG. 15 is a schematic, side elevational view of the end effector of FIGS. 13 and 14, illustrating the scissor blade in an actuated condition.
Figure 16:
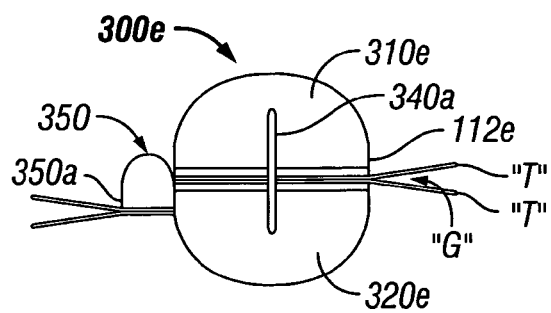
FIG. 16 is a schematic, distal end view of the end effector of FIG. 15.
Figure 17:
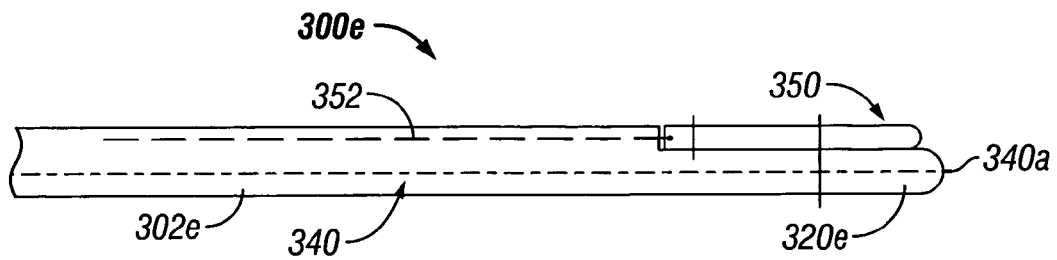
FIG. 17 is a schematic, top plan view of the end effector of FIGS. 13-16.

As seen in FIGS. 13 and 14, scissor blade 350 has a first position in which cutting edge 350a thereof is in substantial registration with gap "G" between jaw members 310e, 320e, or, alternatively, cutting edge 350a of scissor blade 350 is in substantial registration with and/or substantially aligned with the sealing surface 122e of jaw member 310e. As seen in FIGS. 15 and 16, scissor blade 350 has a second position in which cutting edge 350a thereof has been rotated past or beyond gap "G" between jaw members 310e, 320e, to thereby sever or cut tissue "T" extending from therebetween.

End effector assembly 300e may further include a wire 340 extending out of one of jaw members 310e, 320e and anchored to the other of jaw members 310e, 320e. In particular, wire 340 is disposed within central body portion 302e and includes a proximal end (not shown) which connects to an electrosurgical energy source, and a distal end 340a which extends out through fixed jaw member 320e and attaches to a distal end or tip of movable jaw member 310e.

In operation, either prior to, during or following severing of tissue "T" with wire 340, as described above with regard to end effector assemblies 300c or 300d, linkage 352 is actuated (e.g., moved in a proximal direction) to pivot scissor blade 350 about pivot pin 103 and severing tissue "T" along the sides of jaw members 310e, 320e.

Desirably, scissor blade 350 has a length substantially equal to the length of jaw members 310e, 320e. However, it is envisioned that scissor blade 350 may have any length necessary or desired in order to perform the operative procedure.

It is envisioned and within the scope of the present disclosure for the proximal portions of any of the jaw members disclosed above and the distal end of the respective central shafts to be covered by a resilient or flexible insulating material or boot (not shown) to reduce stray current concentrations during electrosurgical activation especially in a monopolar activation mode. As can be appreciated, when jaw members 310, 320 are opened, the boot flexes or expands in certain areas in order to accommodate the movement of jaw members 310, 320. Further details relating to one envisioned insulating boot are described in commonly-owned and concurrently-filed U.S. Provisional Patent Application Ser. No. 60/722,213, filed on Sep. 30, 2005, entitled "INSULATING BOOT FOR ELECTROSURGICAL FORCEPS", the entire contents of which being incorporated by reference herein.

Figure 18:
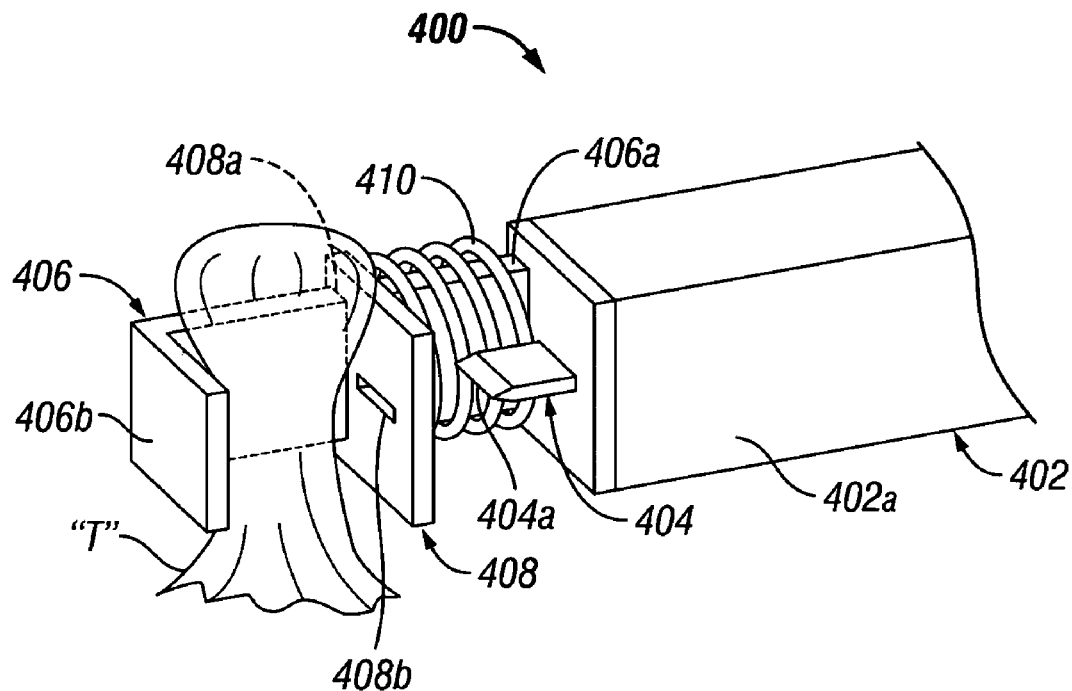
FIG. 18 is a schematic, perspective view of an end effector according to yet another embodiment of the present disclosure, shown in a first condition.
Figure 19:
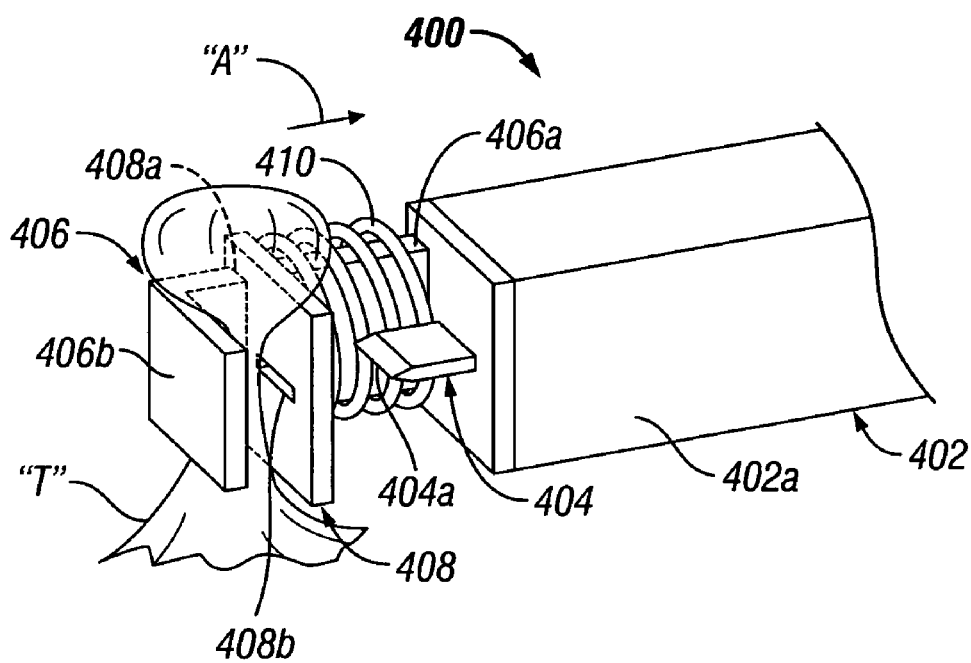
FIG. 19 is a schematic, perspective view of the end effector of FIG. 18, shown in a second condition.
Figure 20:
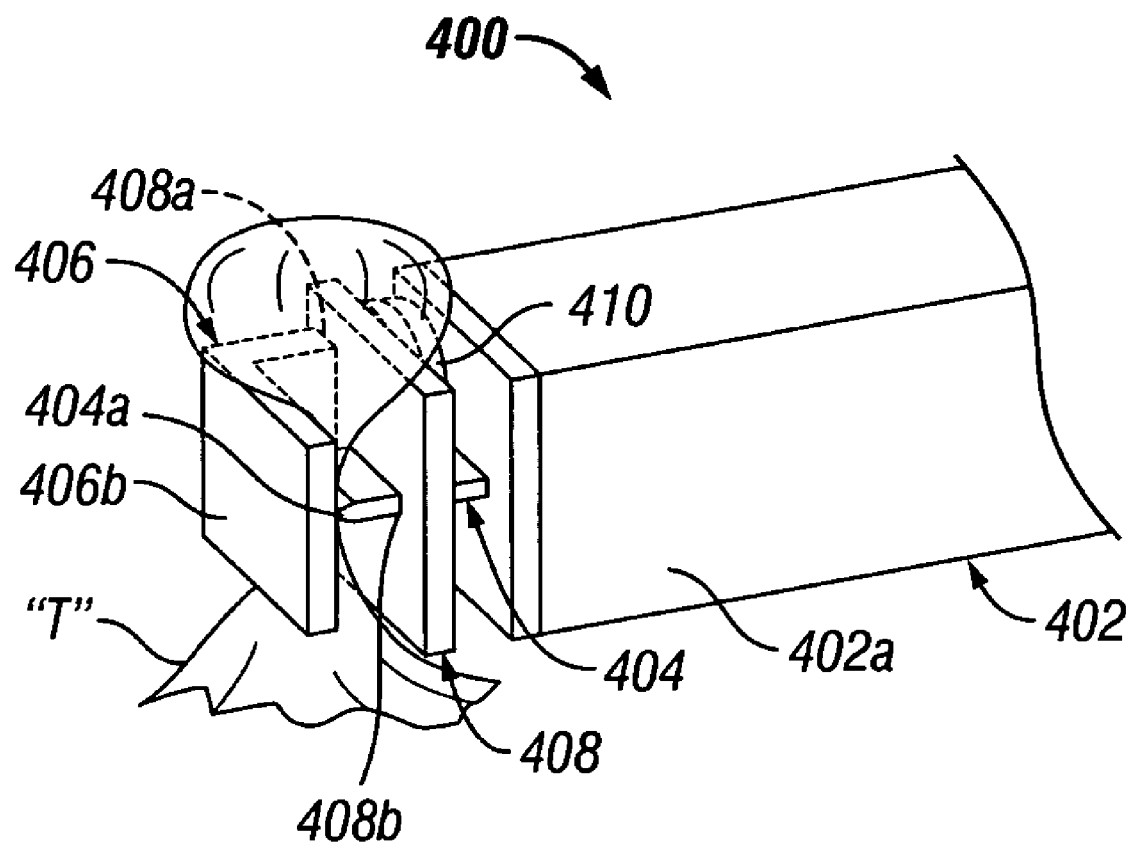
FIG. 20 is a schematic, perspective view of the end effector of FIGS. 18 and 19, shown in a third condition.

Turning now to FIGS. 18-20, an end effector assembly, according to yet another embodiment of the present disclosure, is generally designated as 400. As seen in FIGS. 18-20, end effector assembly 400 includes a central shaft 402 having a distal end 402a configured and adapted to support a cutting blade 404 thereon. It is envisioned that central shaft 402 may be either flexible or rigid along at least a portion of its length.

Cutting blade 404 includes a cutting edge 404a extending in a substantially distal direction. Desirably, cutting edge 404a of cutting blade 404 lies along the central longitudinal axis of central shaft 402.

End effector assembly 400 includes a jaw member 406 movably associated with central shaft 402. In an embodiment, movable jaw member 406 is configured and adapted to translate longitudinally along and/or relative to central shaft 402. Movable jaw member 406 includes a leg portion 406a extending substantially longitudinally along central shaft 402 and a tissue contacting portion 406b extending in a substantially orthogonal direction from a distal end of leg portion 406a. In particular, tissue contacting portion 406b of movable jaw member 406 extends across the central longitudinal axis of central shaft 402 and, more particularly, across cutting blade 404. Reference may be made to commonly-owned and concurrently-filed U.S. Pat. Nos. 6,267,761; and U.S. patent application Ser. No. 09/591,328, filed Jun. 9, 2000; and U.S. patent application Ser. No. 11/170,616, filed on Jun. 29, 2005, the entire contents of which being incorporated by reference herein, for exemplary embodiments and modes of operation of end effector assembly 400.

Jaw member 406 is movable from a position in which tissue contact portion 406b is spaced a distance from cutting edge 404a of cutting blade 404 to a position in which tissue contacting portion 406b is in contact with cutting edge 404a of cutting blade 404.

End effector assembly 400 further includes a floating anvil member 408 interposed between cutting blade 404 and tissue contacting portion 406b of jaw member 406. Anvil member 408 is slidably supported on leg portion 406a of jaw member 406 so that anvil member 408 is translatable along leg portion 406a. In one embodiment, anvil member 408 include a first slot 408a configured and dimensioned to slidably receive leg portion 406a of jaw member 406 therethrough. Anvil member 408 further includes a second or blade slot 408b formed therein that is configured and dimensioned to permit reciprocal movement of cutting blade 404 into and out of blade slot 408b (i.e., through anvil member 408).

End effector assembly 400 further includes a biasing member or spring 410 interposed between cutting blade 404 and anvil member 408. Biasing member 410 is configured so as to maintain anvil member 408 spaced a distance from cutting blade 404. Desirably, biasing member 408 maintains anvil member 408 spaced from cutting blade 404 by an amount sufficient that cutting edge 404a of cutting blade 404 does not extend through blade slot 408b of anvil member 408.

It is envisioned that each of tissue contacting portion 406b and anvil member 408 may be electrically connected to an electrosurgical energy source (not shown) and are provided with elements (not shown) for delivering and/or receiving electrosurgical energy.

With continued reference to FIGS. 18-20, an exemplary method of using a surgical instrument including an end effector assembly 400 is provided. As seen in FIG. 18, with jaw member 406 positioned such that tissue contact portion 406b is spaced a distance from anvil member 408, tissue "T" (e.g., a polyp or the like) in introduced therebetween, either by placing end effector assembly 400 over tissue "T", as shown, or by drawing tissue "T" into the space therebetween.

As seen in FIG. 19, with tissue "T" interposed between tissue contacting portion 406b of jaw member 406 and anvil member 408, jaw member 406 is moved in a proximal direction relative to central shaft 402, as indicated by arrow "A". In so doing, tissue "T" is clamped or grasped between tissue contacting portion 406b of jaw member 406 and anvil member 408. Desirably, a sufficient force is applied to jaw member 406 so as to clamp tissue "T" between tissue contacting portion 406b thereof and anvil member 408 and so as not to substantially move anvil member 408 to compress biasing member 410. As discussed above, biasing member 410 maintains anvil member 408 spaced a distance from cutting blade 404 such that cutting edge 404a does not extend beyond blade slot 408b.

With tissue "T" clamped between tissue contacting portion 406b of jaw member 406 and anvil member 408, an effective amount of electrosurgical energy (e.g., for an effective time period at an effective energy level) is delivered to tissue contacting portion 406b of jaw member 406 and/or anvil member 408 to achieve a desired effect in tissue "T". Desirably, bipolar current is applied to seal the base of the tissue.

As seen in FIG. 20, with tissue "T" treated, jaw member 406 is further advanced in a proximal direction, as indicated by arrow "A", to overcome the bias of biasing member 410 and advance anvil member 408 over cutting blade 404. In so doing, cutting edge 404a of cutting blade 404 severs tissue "T" from the remaining underlying tissue.

In accordance with the present disclosure, any of the end effectors disclosed herein may be configured and adapted to deliver a working pressure of about 3 $kg/cm^2$ to about 16 $kg/cm^2$ and, preferably, of about 7 $kg/cm^2$ to about 13 $kg/cm^2$, to the tissue. By controlling the intensity, frequency and duration of the electrosurgical energy applied to the tissue by the end effector assemblies, the user can cauterize, coagulate/desiccate, seal and/or simply reduce or slow bleeding.

From the foregoing and with reference to the various figure drawings, those skilled in the art will appreciate that certain modifications can also be made to the present disclosure without departing from the scope of the same.

It is also contemplated that the forceps 10 (and/or the electrosurgical generator used in connection with the forceps 10) may include a sensor or feedback mechanism (not shown) that automatically selects the appropriate amount of electrosurgical energy to effectively seal the particularly-sized tissue grasped between the jaw members. The sensor or feedback mechanism may also measure the impedance across the tissue during sealing and provide an indicator (visual and/or audible) that an effective seal has been created between the jaw members. Examples of such sensor systems are described in commonly-owned U.S. patent application Ser. No. 10/427,832 entitled "METHOD AND SYSTEM FOR CONTROLLING OUTPUT OF RF MEDICAL GENERATOR", the entire contents of which being incorporated by reference herein.

It is envisioned that the outer surface of any of the end effector assemblies disclosed herein may include a nickel-based material, coating, stamping, metal injection molding which is designed to reduce adhesion between the jaw members with the surrounding tissue during activation and sealing. Moreover, it is also contemplated that the conductive surfaces of the jaw members may be manufactured from one (or a combination of one or more) of the following materials: nickel-chrome, chromium nitride, MedCoat 2000 manufactured by The Electrolizing Corporation of OHIO, inconel 600 and tin—nickel. The tissue conductive surfaces may also be coated with one or more of the above materials to achieve the same result, i.e., a "non-stick surface". As can be appreciated, reducing the amount that the tissue "sticks" during sealing improves the overall efficacy of the instrument.

One particular class of materials disclosed herein has demonstrated superior non-stick properties and, in some instances, superior seal quality. For example, nitride coatings which include, but are not limited to: TiN, ZrN, TiAlN, and CrN are preferred materials used for non-stick purposes. CrN has been found to be particularly useful for non-stick purposes due to its overall surface properties and optimal performance. Other classes of materials have also been found to reducing overall sticking. For example, high nickel/chrome alloys with a Ni/Cr ratio of approximately 5:1 have been found to significantly reduce sticking in bipolar instrumentation. One particularly useful non-stick material in this class is Inconel 600. Bipolar instrumentation having sealing surfaces 112 and 122 made from or coated with Ni200, Ni201 (~100% Ni) also showed improved non-stick performance over typical bipolar stainless steel electrodes.

Any of the above-described endoscopic forceps and/or end effector assemblies may be incorporated into a catheter-type configuration or other technology suitable for sealing/cutting, such as, for example, E-cutting technology (electrosurgical-cutting technology). Accordingly, any of the above-described endoscopic forceps and/or end effector assemblies may be incorporated into systems, instruments, devices and the like disclosed in U.S. patent application Ser. No. 11/418,876, filed on May 5, 2006, entitled "VESSEL SEALING INSTRUMENT WITH ELECTRICAL CUTTING MECHANISM"; U.S. patent application Ser. No. 10/932,612, filed on Sep. 2, 2004, entitled "VESSEL SEALING INSTRUMENT WITH ELECTRICAL CUTTING MECHANISM"; International Application Ser. No. PCT/US03/28539, filed on Sep. 11, 2003, entitled "ELECTRODE ASSEMBLY FOR SEALING AND CUTTING TISSUE AND METHOD FOR PERFORMING SAME", the entire contents of each of which is herein incorporated by reference.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. An endoscopic forceps for vessel sealing, comprising:
a housing;
a shaft extending from the housing and including a distal end configured and adapted to support an end effector assembly;
an end effector assembly operatively supported on the distal end of the shaft, the end effector assembly including:
a pair of jaw members each pivotally connected about a pivot pin, the pair of jaw members movable from a first position in spaced relation relative to one another to at least a second position closer to one another for grasping tissue therebetween, each of the jaw members adapted to connect to an electrosurgical energy source such that the pair of jaw members are capable of conducting energy through tissue held therebetween to affect a tissue seal;
an outer sleeve translatably disposed about the shaft, wherein the sleeve has a first position in which the sleeve does not cover the pair of jaw members about the pivot pin, wherein the pivot pin is disposed beyond a distal end of the outer sleeve to thereby permit selective movement of both jaw members to a substantially orthogonal orientation relative to the shaft, and at least one second position in which the sleeve covers at least a portion of the pair of jaw members about the pivot pin, wherein the pivot pin is disposed within the outer sleeve to thereby align the jaw members within the shaft; and
a linkage operatively connected to at least one of the pair of jaw members, the linkage being actuatable to initially move the jaw members to a substantially orthogonal position relative to the shaft and subsequently movable to pivot each jaw member relative to one another to grasp tissue therebetween; and
a movable handle operatively associated with the housing, wherein actuation of the movable handle relative to the housing results in movement of the jaw members to advance the jaw members relative to the outer sleeve and to pivot the jaw members about the pivot pin when disposed at a position beyond the distal end of the outer sleeve.

2. The endoscopic forceps according to claim 1, wherein the pair of jaw members are biased to the first position.

3. The endoscopic forceps according to claim 2, wherein the pair of jaw members operate unilaterally.

4. The endoscopic forceps according to claim 2, wherein the pair of jaw members operate bilaterally.

5. The endoscopic forceps according to claim 4, wherein the end effector assembly includes at least one stop member disposed on an inner facing surface of at least one of the pair of jaw members.

6. The endoscopic forceps according to claim 5, wherein the end effector assembly delivers a working pressure of from about 3 kg/cm$^2$ to about 16 kg/cm$^2$.

7. The endoscopic forceps according to claim 5, wherein the end effector assembly delivers a working pressure of from about 7 kg/cm$^2$ to about 13 kg/cm$^2$.

8. The endoscopic forceps according to claim 4, wherein the pair of jaw members are pivotable to a substantially orthogonal orientation relative to a longitudinal axis of the shaft.

9. The endoscopic forceps according to claim 1, wherein the shaft and outer sleeve are at least partially flexible.

* * * * *